(12) United States Patent
Lin et al.

(10) Patent No.: US 6,677,377 B2
(45) Date of Patent: Jan. 13, 2004

(54) STRUCTURE BASED DISCOVERY OF INHIBITORS OF MATRIPTASE FOR THE TREATMENT OF CANCER AND OTHER CONDITIONS

(75) Inventors: Chen-Yong Lin, Falls Church, VA (US); Robert B. Dickson, Kensington, MD (US); Shaomeng Wang, Rockville, MD (US); Istvan Enyedy, Hamden, CT (US); Sheau-Ling Lee, Falls Church, VA (US)

(73) Assignee: Georgetown University School of Medicine, Washington, DC (US)

( * ) Notice: Subject to any disclaimer, the term of this patent is extended or adjusted under 35 U.S.C. 154(b) by 0 days.

(21) Appl. No.: 09/885,295

(22) Filed: Jun. 21, 2001

(65) Prior Publication Data

US 2003/0092752 A1 May 15, 2003

Related U.S. Application Data

(60) Provisional application No. 60/213,073, filed on Jun. 21, 2000.

(51) Int. Cl.[7] .............................................. A61K 31/155
(52) U.S. Cl. ..................................................... 514/636
(58) Field of Search .......................................... 514/636

(56) References Cited

U.S. PATENT DOCUMENTS

| | | | | |
|---|---|---|---|---|
| 4,933,347 A | * | 6/1990 | Tidwell et al. | 514/256 |
| 4,963,589 A | * | 10/1990 | Tidwell et al. | 514/636 |
| 5,162,361 A | * | 11/1992 | Rosenthal et al. | 514/396 |
| 6,046,226 A | * | 4/2000 | Dykstra et al. | 514/394 |

OTHER PUBLICATIONS

Bailly et al, Biochem. J. vol. 323, pp. 23–31 (1997).*
Enyedy et al, J. Med. Chem., vol. 44, pp. 1349–1355 (2001).*

* cited by examiner

*Primary Examiner*—James H. Reamer
(74) *Attorney, Agent, or Firm*—Pillsbury Winthrop LLP

(57) ABSTRACT

The present invention relates to a method of inhibiting carcinoma progression wherein matriptase plays a role in a subject in need of such inhibition including administering to a subject an effective amount of a compound comprising two positively charged groups, which are the same or different. The groups are linked by a chemical group having a length of between 5 and 30 A, and preferably between 15 and 24 A. Diagnostic methods based on matriptase action and therapeutic methods involving inhibition of matriptase activity are provided.

23 Claims, 10 Drawing Sheets

(A)

(B)

(A)

(B)

(A)

(B)

STRUCTURE BASED DISCOVERY OF INHIBITORS OF MATRIPTASE FOR THE TREATMENT OF CANCER AND OTHER CONDITIONS

CROSS REFERENCE TO RELATED APPLICATION

This application claims priority from U.S. Provisional Ser. No. 60/213,073, filed Jun. 21, 2000, and is incorporated herein by reference in its entirety.

BACKGROUND OF THE INVENTION

1. Field of the Invention

The present invention relates to methods for diagnosing and treating conditions involving matriptase activity, particularly cancer. In particular, the invention is based on the elucidation of matriptase activity and involvement in the development of precancerous and cancerous conditions. More particularly, the invention relates to the design of bioassay testing methods for cancer diagnosis based on the detection of matriptase activity, identification of compounds capable of inhibiting matriptase activity and design of cancer therapy protocols based on the inhibition of matriptase employing small molecule inhibitors.

2. Discussion of the Related Art

Serine Proteases and Other Cancer Related Proteases. Elevated proteolytic activity has been implicated in neoplastic progression. While the exact role(s) of proteolytic enzymes in the progression of tumor remains unclear, it seems that proteases may be involved in almost every step of the development and spread of cancer. A widely proposed view is that proteases contribute to the degradation of extracellular matrix (ECM) and to tissue remodeling, and are necessary for cancer progression and metastasis. A wide array of ECM-degrading proteases has been discovered, the expression of some of which correlates with tumor progression. These include matrix metalloproteases (MMPS) family, plasmin/urokinase type plasminogen activator system and lysosomal proteases cathepsins D and B reviewed by Mignatti et al., *Physiol. Rev.* 73: 161–95 (1993). The plasmin/urokinase type plasminogen activator system is composed of plasmin, the major ECM-degrading protease; the plasminogen activator, uPA; the plasmin inhibitor α2-anti-plasmin, the plasminogen activator inhibitors PAI-1 and PAI-2; and the cell membrane receptor for uPA (uPAR) (Andreasen et al., *Int. J. Cancer* 72: 1–22 (1997)).

The MMPs are a family of zinc-dependent enzymes with characteristic structures and catalytic properties. The plasmin/urokinase type plasminogen activator system and the 72-kDa gelatinase (MMP-2)/membrane-type MMP system have received the most attention for their potential roles in the process of progression of breast cancer and other carcinomas. However, both systems appear to require indirect mechanisms to recruit and activate the major ECM-degrading proteases on the surface of cancer cells. For example, uPA is produced in vivo (Nielson et al., *Lab. Invest.* 74: 168–77 (1996); Pyke et al., *Cancer Res.* 53: 1911–15 (1993); Polette et al., *Virchows Arch.* 424: 641–45 (1994); and Okada et al., *Proc. Natl. Acad. Sci. USA* 92: 2730–34 (1995)) in human breast carcinomas by myofibroblasts adjacent to cancer cells and must diffuse to the cancer cells for receptor-mediated activation and presentation on the surfaces of cancer cells. However, the uPA receptor (uPAR) is detected in macrophages that infiltrate tumor foci in ductal breast cancer. Somewhat analogously, the majority of the MMP family members, such as 72-kDa/Gelatinase A (MMP-2) (Lin et al., *J. Biol. Chem.* 272: 9147–52 (1997)), stromelysin-3 (MMP-11) (Matsudaira, *J. Biol. Chem.* 262: 10035–38 (1987)), MTMMP (MMP-14), are expressed by fibroblastic cells of tumor stroma, or surrounding noncancerous tissues, or both. Indirect mechanisms of activation and recruitment of Gelatinase A in the close vicinity of the surfaces of cancer cells have been proposed, such that an unidentified cancer cell-derived membrane receptor(s) of Gelatinase A could serve as membrane anchor for Gelatinase A; cleaved MT-MMP from stroma cells could then diffuse to the surfaces of cancer cells to activate Gelatinase A. Matrilysin (MMP-7; Pump-1) appears to be the only MMP which is found predominantly in the epithelial cells.

The stromal origins of these well-characterized extracellular matrix-degrading proteases may suggest that cancer progression is an event which either depends entirely upon stromal-epithelial cooperation or which is controlled by some other unknown epithelial-derived proteases. Search for these epithelial-derived proteolytic systems that may interact with plasmin/urokinase type plasminogen activator system and/or with MMP family could provide a missing link in the understanding of malignant progression.

Matriptase was initially identified from T-47D human breast cancer cells as a major gelatinase with a migration rate between those of Gelatinase A (72-kDa, MMP-2) and Gelatinase B (92-kDa, MMP-9). It has been proposed to play a role in the metastatic invasiveness of breast cancer. (See U.S. Pat. No. 5,482,848, the contents of which are incorporated herein by reference in their entirety.) The primary cleavage specificity of matriptase was identified to be arginine and lysine residues, similar to the majority of serine proteases, including trypsin and plasmin. In addition, matriptase, like trypsin, exhibits broad spectrum cleavage activity, and such activity is likely to contribute to its gelatinolytic activity. The trypsin-like activity of matriptase distinguishes it from Gelatinases A and B, which may cleave gelatin at glycine residues, the most abundant (almost one third) of amino acid residues in gelatin.

Kunitz-Type Serine Protease Inhibitors. Hepatocyte growth factor (HGF) activator inhibitor-1 (HAI-1) is a Kunitz-type serine protease inhibitor which is able to inhibit HGF activator, a blood coagulation factor XII-like serine protease. The mature form of this protease inhibitor has 478 amino acid residues, with a calculated molecular mass of 53,319. A putative transmembrane domain is located at its carboxyl terminus. HAI-1 contains two Kunitz domains (domain I spans residues 246–306; domain II spans residues 371 to 431) separated by a LDL receptor domain (residues 315 to 360). The presumed P1 residue of active-site cleft is likely to be arginine-260 in Kunitz domain I and lysine 385 in domain II by alignment with bovine pancreatic trypsin inhibitor (BPTI, aprotinin) and with other Kunitz-type inhibitors. Thus, HAI-1 has specificity against trypsin-type proteases. Although HGF activator is exclusively expressed by liver cells, HAI-1 was originally purified from the conditioned media of carcinoma cells as a 40-kDa fragment doublet, rather than the proposed, mature, membrane-bound, 53-kDa form (Shimomura et al., *J. Biol. Chem.* 272: 6370–76 (1997)).

The protein inhibitors of serine proteases can be classified into at least 10 families, according to various schemes. Among them, serpins, such as maspin (Sheng et al., *Proc. Natl. Acad. Sci. USA* 93: 11669–74 (1996)) and Kunitz-type inhibitors, such as urinary trypsin inhibitor (Kobayashi et al., *Cancer Res.* 54: 844–49 (1994)) have been previously implicated in suppression of cancer progression. The Kunitz-type inhibitors form very tight, but reversible complexes with their target serine proteases. The reactive sites of these inhibitors are rigid and can simulate optimal protease substrates. The interaction between a serine protease and a Kunitz-type inhibitor depends on complementary, large surface areas of contact between the protease and inhibitor. The inhibitory activity of the recovered Kunitz-type inhibitor from protease complexes can always be reconstituted. The Kunitz-type inhibitors may be cleaved by cognate proteases, but such cleavage is not essential for their inhibitory activity. In contrast, serpin-type inhibitors also form tight, stable complexes with proteases; in most of cases these complexes are even more stable than those containing Kunitz-type inhibitors. Cleavage of serpins by proteases is necessary for their inhibition, and serpins are always recovered in a cleaved, inactive form from protease reactions.

Thus, serpins are considered to be suicide substrate inhibitors, and their inhibitory activity will be lost after encounters with proteases. The suicide nature of serpin inhibitors may result in regulation of proteolytic activity in vivo by direct removal of unwanted proteases via other membrane-bound endocytic receptors (in the case of uPA inhibitors). However, the Kunitz type inhibitors may simply compete with physiological substrates (such as ECM components), and in turn, reduce their availability for proteolysis. These differences may result in different mechanisms whereby these proteases perform their roles in ECM-degradation and cancer progression.

It has previously been disclosed that a soybean-derived compound known as Bowman-Birk inhibitor (BBI, from Sigma) may have anti-cancer activity by preventing tumor initiation and progression in model systems. However, due to its size and non-synthetic nature, use of BBI in therapeutic methods based on inhibition of matriptase activity can be cumbersome and expensive.

For their stability and permeability, small molecule inhibitors provide valuable tools on functional studies in various systems. It is highly desirable to provide small molecules that can inhibit matriptase activity. Based on the potential effects thereof on carcinoma progression, cell migration, proliferation and apoptosis, it would be beneficial if compounds could be obtained which selectively block the proteolytic activity of matriptase. More specifically, it would be beneficial if compounds could be obtained which antagonize cascade protease activators produced by cleavage of matriptase substrates. Such compounds have significant therapeutic potential, in particular for treatment of cancer and other conditions involving carcinoma progression and migration and abnormal cell differentiation and proliferation. Compounds having improved selectivity, solubility and stability are particularly desirable.

SUMMARY AND OBJECTS OF THE INVENTION

In one embodiment, the present invention provides a method of inhibiting carcinoma progression wherein matriptase plays a role in a subject in need of such inhibition comprising administering to a subject an effective amount of a compound comprising two groups capable of being positively charges at physiological pH, which are the same or different. The groups are linked by a chemical group having a length of between 5 and 30 Å, and preferably between 15 and 24 Å. The groups are preferably selected from the following groups:

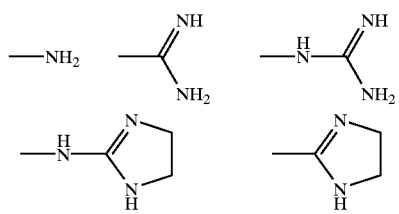

Preferred compounds include the compounds of Formulas I through VI which have the structures corresponding to formulae I–VI below, wherein X and Y can be any substituents.

FORMULA I

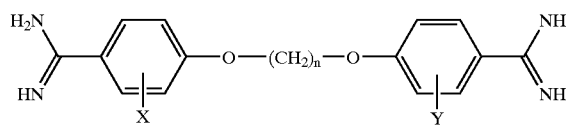

FORMULA II

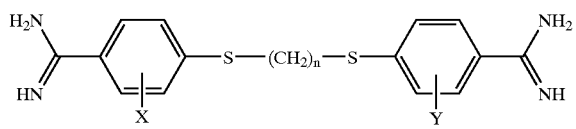

FORMULA III

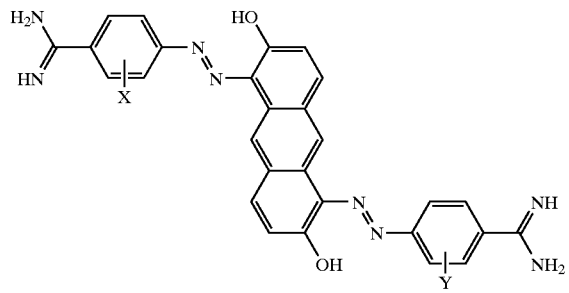

FORMULA IV

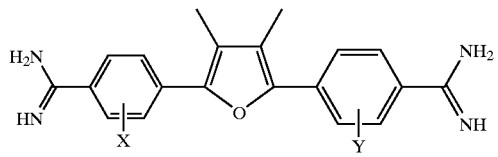

FORMULA V

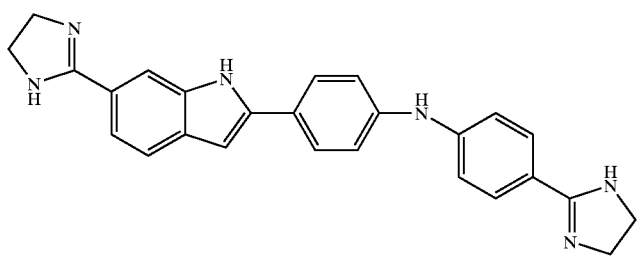

FORMULA VI

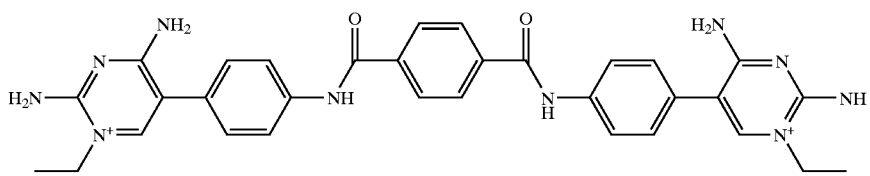

In another embodiment, the present invention provides a method of inhibiting carcinoma progression wherein matriptase plays a role in a subject in need of such inhibition comprising administering to a subject an effective amount of a compound selected from the group consisting of compounds A, B, C, D, E, F, G and analogs thereof. Compounds A, B, C, D, E, F and G have the following respective structures:

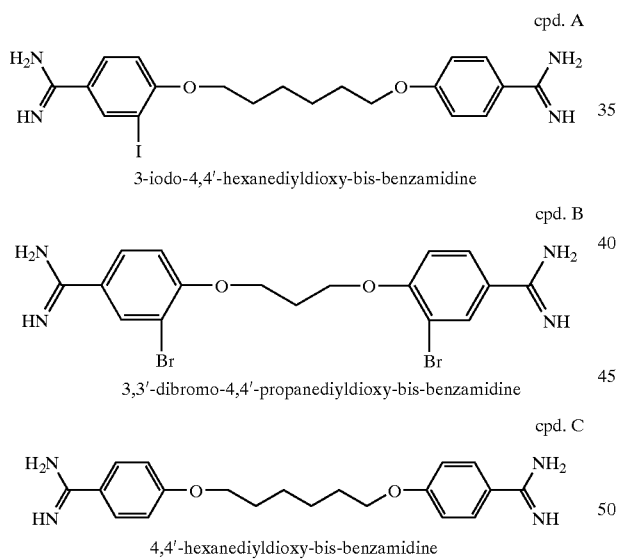

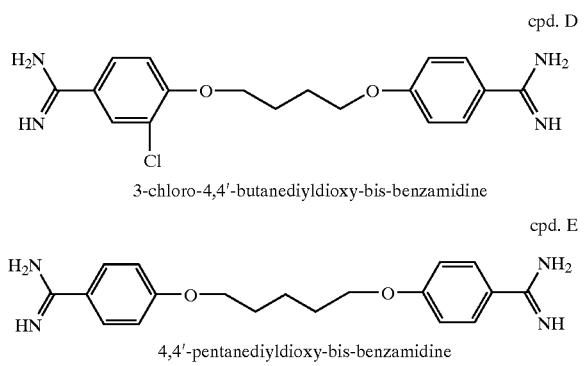

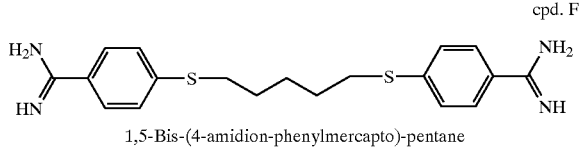

1,5-Bis-(4-amidion-phenylmercapto)-pentane cpd. G

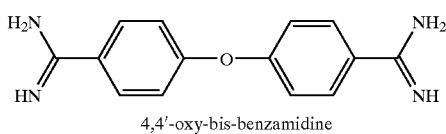

4,4'-oxy-bis-benzamidine

In another embodiment, the invention provides a method of treating malignancies, pre-malignant conditions, and pathologic conditions in a subject which are characterized by the expression of single-chain (zymogen) and/or two-chain (activated) form of matriptase comprising administering a therapeutically effective amount of a compound selected from the group consisting of compounds A, B, C, D, E, F, G and analogs thereof.

In yet another embodiment, the invention provides a method of therapy which results in the inhibition of matriptase in a subject in need of such inhibition which comprises administering a therapeutically effective amount of at least one compound selected from the group consisting of compounds A, B, C, D, E, F, G and analogs thereof:

cpd. A

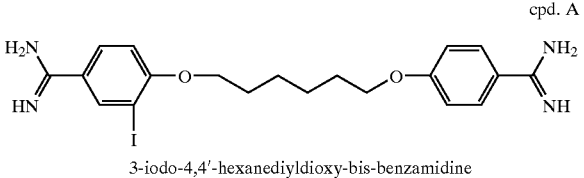

3-iodo-4,4'-hexanediyldioxy-bis-benzamidine cpd. B

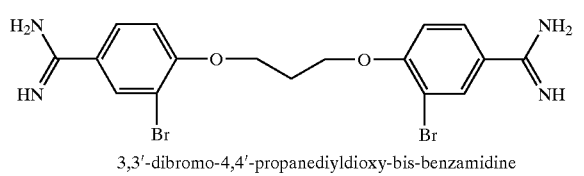

3,3'-dibromo-4,4'-propanediyldioxy-bis-benzamidine

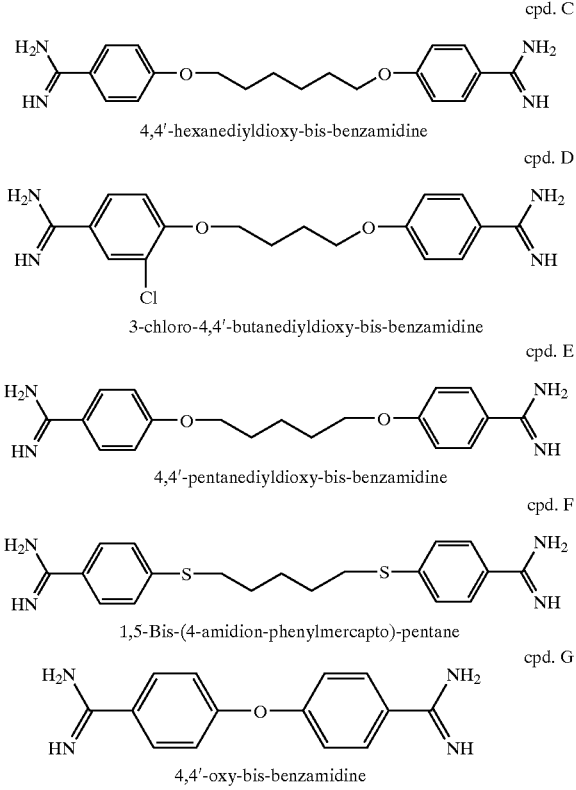

cpd. C
4,4'-hexanediyldioxy-bis-benzamidine cpd. D
3-chloro-4,4'-butanediyldioxy-bis-benzamidine cpd. E
4,4'-pentanediyldioxy-bis-benzamidine cpd. F
1,5-Bis-(4-amidion-phenylmercapto)-pentane cpd. G
4,4'-oxy-bis-benzamidine In still another embodiment, the invention provides a method of treating cancer comprising administering a therapeutically effective amount of at least one compound selected from the group consisting of compounds A, B, C, D, E, F, G and analogs thereof.

In a further embodiment, the invention provides a method of diagnosing cancer comprising exposing a tissue sample to an antibody or immunogenic fragment thereof which recognizes and binds to a product of matriptase mediated proteolysis of a matriptase substrate.

In another embodiment, the invention provides an in vivo method of diagnosing the presence of a pre-malignant lesion, a malignancy or other pathologic condition in a subject comprising the steps of:

(A) administering to a subject, that is to be tested for a pre-malignant or malignant lesion, or other pathologic condition, which is characterized by the presence of a product of matriptase mediated proteolysis of a substrate of matriptase, a labeled agent which recognizes and binds to the product of matriptase mediated proteolysis; and (B) imaging the subject for the localization of the labeled agent.

In still another embodiment, the invention provides an in vitro method of diagnosing the presence of a pre-malignant lesion, a malignancy, or other pathologic condition, in a subject, which is characterized by the presence of a product of matriptase mediated proteolysis of a substrate of matriptase comprising the steps of:

(A) obtaining a biological sample from a subject that is to be tested for a pre-malignant lesion, a malignancy, or other pathologic condition;

(B) exposing the biological sample to a labeled agent which recognizes and binds to the product of matriptase mediated proteolysis; and (C) determining whether said labeled agent bound to the biological sample.

BRIEF DESCRIPTION OF THE DRAWINGS

FIG. 1A shows the silver-stained protein patterns of HGF incubated overnight without (0) or with increasing amount of matriptase ( ); FIG. 1B shows Western immunoblot. HGF incubated overnight without (−) or with (+) matriptase was immunoblotted with anti-__HGF (__chain) or anti-__-HGF (__chain);

FIG. 5A shows how single-chain pro-uPA is converted into two-chain form uPA by matriptase; wherein pro-uPA was incubated overnight active matriptase in the absence (0) or presence of increasing amount of matriptase ( ); the cleaved products were analyzed by electrophoresis followed by silver-staining; and FIG. 5B shows how matriptase cleavage of pro-uPA generates an active protease; pro-uPA was either incubated for 30 min with matriptase (closed circles) or incubated 1 min with plasmin (opened circles) prior to the assay, plasmin (opened triangles), uPA (closed triangles), and matriptase (closed squares) all exhibit low activity;

DETAILED DESCRIPTION OF THE INVENTION

Figure 1A:
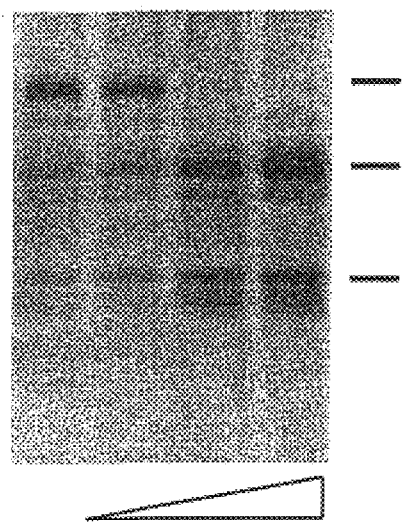
FIGS. 1A and 1B show how matriptase converts single-chain HGF into smaller fragments, which can be recognized by anti-__-chain HGF and __-chain HGF antibodies.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

Definitions

By "matriptase" is meant a trypsin-like protein, with a molecular weight of between 72-kDa and 92-kDa and is related to SEQ ID NO: 4 or is a fragment thereof. It can include both single-chain and double-chain forms of the protein. The zymogen form (inactive form) of matriptase is a single-chain protein. The two-chain form of matriptase is the active form of matriptase, which possesses catalytic activity. Both forms of matriptase are found to some extent in milk and cancer cells because extracellular matrix (ECM) remodeling is necessary to both normal and pathologic remodeling processes. Both cancer cells and milk contain the different forms of matriptase. However, in milk the dominant form is the activated form of matriptase which then binds to HAI-1.

By "matriptase modulating compound" or "matriptase modulating agent" is meant a reagent which regulates, preferably inhibits the activation of matriptase (e.g., cleavage of the matriptase single-chain zymogen to the active two-chain moiety) or the activity of the two-chain form of matriptase. This inhibition can be at the transcriptional, translation, and/or post-translational levels. Additionally, modulation of matriptase activity can be via the binding of a compound to the zymogen or activated forms of matriptase.

By "matriptase expressing tissue" is meant any tissue which expresses any form of matriptase, either malignant, pre-malignant, normal tissue, or tissue which is subject to another pathologic condition.

By "malignancy" is meant to refer to a tissue, cell or organ which contains a neoplasm or tumor that is cancerous as opposed to benign. Malignant cells typically involve growth that infiltrates tissue (e.g., metastases). By "benign" is meant an abnormal growth which does not spread by metastasis or infiltration of the tissue. The malignant cell of the instant invention can be of any tissue; preferred tissues are epithelial cells.

By "tumor progression" or "tumor metastasis" is meant the ability of a tumor to develop secondary tumors at a site remote from the primary tumor. Tumor metastasis typically requires local progression, passive transport, lodgement and proliferation at a remote site. This process also requires the development of tumor vascularization, a process termed angiogenesis. Therefore, by "tumor progression" and "metastasis," we also include the process of tumor angiogenesis.

By "pre-malignant conditions" or "pre-malignant lesion" is meant a cell or tissue which has the potential to turn malignant or metastatic, and preferably epithelial cells with said potential. Pre-malignant lesions include, but are not limited to: atypical ductal hyperplasia of the breast, actinic keratosis (AK), leukoplakia, Barrett's epithelium (columnar metaplasia) of the esophagus, ulcerative colitis, adenomatous colorectal polyps, erythroplasia of Queyrat, Bowen's disease, bowenoid papulosis, vulvar intraepithelial neoplasia (VIN), and displastic changes to the cervix.

By "other condition" or "pathologic conditions" is meant any genetic susceptibility or non-cancerous pathologic condition relating to any disease susceptibility or diagnosis.

By "tumor formation-inhibiting effective amount" is meant an amount of a compound, which is characterized as inhibiting activation of matriptase or matriptase activity, and which when administered to a subject, such as a human subject, prevents the formation of a tumor, or causes a preexisting tumor, or pre-malignant condition, to enter remission. This can be assessed by screening a high-risk patient for a prolonged period of time to determine that the cancer does not arise and/or the pre-malignant condition is reversed. This also can be assessed by imaging of the subject with a tumor to determine whether the mass of the tumor is shrinking. A tumor formation-inhibiting effective amount also includes an amounts which provides ameliorative to relief to the subject. The tumor formation-inhibiting effective amount can also be assessed based on its effect on blood circulation of inhibitors, such as BBIC. Preferred tumor formation-inhibiting effective amounts of agents such as BBIC are in the range of 100 $\mu$g/kg to 20 mg/kg body weight of the subject. More preferred ranges include 1 $\mu$g/kg to 10 mg/kg body weight of the subject.

By "labeling agent" is meant to include fluorescent labels, enzyme labels, and radioactive labels. By "radiolabel" or "radioactive label" is meant any radioisotope for use in humans for purposes of diagnostic imaging. Preferred radioisotopes for such use include: $^{67}$Cu, $^{67}$Ga, $^{99}$Te, $^{131}$I, $^{123}$I, $^{125}$I, $^{111}$In, $^{188}$Re, $^{186}$Re and $^{90}$Y. By "fluorescent label" is meant any compound used for screening samples (e.g., tissue samples and biopsies) which emits fluorescent energy. Preferred fluorescent labels include fluorescein, rhodamine and phycoerythrin.

By "biological sample" is meant a specimen comprising body fluids, cells or tissue from a subject, preferably a human subject. Preferably the biological sample contains cells, which can be obtained via a biopsy or a nipple aspirate, or are epithelial cells. The sample can also be body fluid that has come into contact, either naturally or by artificial methods (e.g. surgical means), a malignant cell or cells of a pre-malignant lesion.

By "matriptase expressing tissue" is meant any biological sample comprising one or more cells which expresses a form or forms of matriptase.

By "subject" is meant an animal, preferably mammalian, and most preferably human.

By "immunogenic fragment" is meant a portion of a matriptase protein which induces humoral and/or cell-mediated immunity but not immunological tolerance.

By "epitope" is meant a region on an antigen molecule (e.g., matriptase) to which an antibody or an immunogenic fragment thereof binds specifically. The epitope can be a three dimensional epitope formed from residues on different regions of a protein antigen molecule, which, in a native state, are closely apposed due to protein folding. "Epitope" as used herein can also mean an epitope created by a peptide or hapten portion of matriptase and not a three dimensional epitope.

As used herein, the term "antibody" is meant to refer to complete, intact antibodies, and Fab fragments and F(ab)$_2$ fragments thereof. Complete, intact antibodies include monoclonal antibodies such as murine monoclonal antibodies (mAb), chimeric antibodies and humanized antibodies. The production of antibodies and the protein structures of complete, intact antibodies, as well as antibody fragments (e.g., Fab fragments and F(ab)$_2$ fragments) and the organization of the genetic sequences that encode such molecules are well known and are described, for example, in Harlow et al., ANTIBODIES: A Laboratory Manual, Cold Spring Harbor Laboratory, Cold Spring Harbor, N.Y. (1988).

Local invasion and metastasis of cancers have been proposed to require imbalanced or unregulated expression of proteases, such as metalloproteases and urokinase-type plasminogen activator (uPA), at invading edges of carcinoma cells[1-5]. In recent years, increasing efforts have been applied to the development of potent and selective inhibitors of these proteases as potential anticancer therapeutic agents[6-8]. Accordingly, a number of metalloprotease inhibitors are now in clinical trial for the treatment of cancer[7].

However, both metalloproteases and urokinase are mostly synthesized in the tumor stroma and require indirect mechanisms for their recruitment and activation on the surfaces of cancer cells[1]. We have recently characterized a novel, integral membrane serine protease, matriptase (GenBank accession number AF 118224), and its cognate inhibitor as HAI-1 (hepatocyte growth factor activator inhibitor 1)[9-11]. In contrast to most other protease-inhibitor systems, both matriptase and HAI-1 are selectively expressed by cultured breast epithelial cells and cancer cells, but not by fibroblasts nor by fibrosarcoma cells. In addition to the C-terminal serine protease domain, the N-terminal non-catalytic region of matriptase contains two tandem repeats of a CUB (C1r/s, Uegf and Bone morphogenetic protein-1) domain and four tandem repeats of a low density lipoprotein receptor domain that are likely to be involved in protein—protein interaction[10]. Immunofluorescent staining of cultured breast cancer cells demonstrated that matriptase is concentrated on the cell peripheries at pseudopodia and on membrane-ruffles in spreading cells[9]. Of particular interest, matriptase has recently been shown to activate hepatocyte growth factor and single-chain urokinase plasminogen activator[5; 12]. Recently, a large peptide inhibitor of matriptase, ecotin, has been described; this protease inhibitor retards the growth of PC-3 prostate cancer tumors in nude mice further suggesting that matriptase may be involved in cancer progression[13]. Taken together, these data suggest that matriptase may be a central regulator of cell migration and cancer invasion, and may provide a novel cancer-associated protease target for design of new anti-cancer drugs.

The present invention is based on the discovery and development of potent and selective small molecule inhibitors of matriptase. A potent, selective, non-peptide and drug-like small molecule matriptase inhibitor will not only be useful as a pharmacological tool to further elucidate the biological functions of matriptase, but also may have the therapeutic potential for the treatment of cancer through stopping invasion and metastasis. Although large peptide matriptase inhibitors, such as ecotin, have been reported, drug-like, small molecule matriptase inhibitors are currently not available. Herein, we report our discovery of bis-benzamidines as a class of matriptase inhibitors through structure-based database search.

The present invention is based on recent discoveries relating to a novel serine protease system, matriptase and its cognate inhibitor (the hepatocyte growth factor activator inhibitor 1). Considering its unique characteristics: the epithelial and cancer cells origin, the membrane integral property, and the multiple putative regulatory domains, the invention is generally based on the hypothesis that matriptase functions as an upstream activator in matrix progression. In particular, the present invention is based on the discovery that matriptase can convert single chain hepatocyte growth factor/scatter factor precursor to the active factor that can induce scatter of Madin-Darby canine kidney epithelial cells and can activate c-Met tyrosine phosphorylation in A549 human lung carcinoma cells. In addition, it has been discovered that matriptase can activate urokinase plasminogen activator but not plasminogen.

While the foregoing detailed description is focused on methods for diagnosing cancer, particularly breast cancer, the subject invention is directed to all conditions wherein matriptase plays a role.

The invention provides novel cancer diagnosis and therapy methods based in part on a novel mechanism in the epithelial-mensenchymal interaction that an epithelial membrane activator regulates the activation of the stromal-origin factors in the extracellular matix degradation and in the cell migration. These observations provide a possible direct link that has been missing from current model of tissue remodeling.

Identification of a Mechanism Associated with Matriptase Activity

The present inventors have conduced extensive research the initial results of which allowed for the discovery of matriptase and the elucidation of some aspects of its activity. The discoveries associated with matriptase have been incorporated in a research program aimed at providing diagnosis and therapy protocols for the treatment of various cancers, particularly breast cancer. These protocols are based in part on the elucidation of the mechanistic aspects associated with matriptase activity and the utilization of computer modeling tools in combination with biological testing in the identification of antibody diagnostic agents and small molecule matriptase inhibitors as therapeutic agents.

Matriptase is a trypsin-like serine protease with two regulatory modules: two tandem repeats of the complement subcomponent C1r/s domain and four tandem repeats of LDL receptor domain (Lin et al., *J. Biol. Chem.* 274: 18231–6 (1999)). In order to evaluate the role of matriptase in physiological conditions, its expression in human milk was studied. It was found that milk-derived matriptase strongly interacts with fragments of HAI-1 to form SDS-stable complexes.

The mosaic protease is characterized by trypsin-like activity and two regulatory modules (e.g., LDL receptor and complement subcomponent C1r/s domains). Matriptase was initially purified from T-47D human breast cancer cells.

In breast cancer cells, matriptase was detected mainly as an uncomplexed form; however, low levels of matriptase were detected in SDS-stable, 110- and 95-kDa complexes that could be dissociated by boiling. In striking contrast, only the complexed matriptase was detected in human milk.

The complexed matriptase has now been purified by a combination of ionic exchange chromatography and immunoaffinity chromatography. Amino acid sequences obtained from the matriptase-associated proteins reveal that they are fragments of an integral membrane, Kunitz-type serine protease inhibitor that was previously reported to be an inhibitor (termed HAI-1) of hepatocyte growth factor activator.

In addition, matriptase and its complexes were also detected in four milk-derived, SV-40 T-antigen-immortalized mammary luminal epithelial cell lines, but not in two human foreskin fibroblasts nor in HT1080 fibrosarcoma cell line. The milk-derived matriptase complexes are likely to be produced by the epithelial components of lactating mammary gland in vivo, and the activity and function of matriptase may be differentially regulated by its cognate inhibitor, comparing breast cancer with the lactating mammary gland.

It has now been discovered that matriptase and its cognate Kunitz-type serine protease inhibitor can be characterized as an extracellular, trypsin-like protease system. In vivo expression of matriptase and its inhibitor was observed in breast cancer cells, breast epithelial cells, and in other human carcinomas including ovarian, endometrial, and colon. In no case were matriptase or the inhibitor found in fibroblasts or fibrosarcomas. Matriptase is a type 2 integral membrane serine protease that contains tandem repeats of putative regulatory domains: the LDL receptor domains and the CUB (C1r/s, Uegf and Bone morphogenetic protein-1) domains (also see updated sequence in the GenBank/EBI Data Bank with accession number AF118224).

The cognate inhibitor of matriptase is a type 1 integral membrane protein containing two Kunitz domains separated by a LDL receptor domain.

Although originally isolated from breast cancer cell conditioned medium and human milk, both matriptase and the inhibitor are also found on cell surface, mostly by anchoring in the membrane through their transmembrane domains. The soluble form matriptase is likely to be resulted from the shedding of the surface-bound matriptase.

These characteristics of matriptase suggest that this protease is involved in cell migration and progression by acting as a direct upstream regulator. Without wishing to be bound by any particular theory, it is believed that matriptse is presented on the tumor or epithelial cell surface and interacts with a variety of factors and digests a broad range of substrates. These actions, together, may induce dramatic changes in the extracellular environment and in the surrounding cells contributing to cell migration, progression, and metastasis.

To further elucidate the biological roles of matriptase, the substrates of this protease were investigated. Particular attention was dircted at HGF. HGF, also known as scatter factor (SF), was originally identified as a potent mitogen for mature hepatocytesand as a fibroblast-derived factor with the ability to induce scattering of epithelial colonies. HGF/SF can stimulate cell motility, and induce morphogenesis. Although other factors such as blood coagulation factor XIIa, HGF activator, uPA, and tPA have been reported to be able to activate HGF/SF, no epithelial-origin activator has been reported.

Our interest on HGF/SF was further stimulated by the fact that the endogenous kunitz-type inhibitor of matriptase is the HGF activator inhibitor 1 (HAI-1).

In elucidating the mechanisms of matriptase action, the following methods and materials were emplyed:

Antibodies__Polyclonal antibodies to hepatocyte growth factor (HGF)__-chain (C-20) and __chain (N-19) were purchased from Santa Cruz Biotechnology (Calne, Wilshire, U.K). Monoclonal anti-human Met antibodies (clones DL-21 and DL-24) were purchased from Upstate (Lake Placid, N.Y.). The recombinant anti-phosphotyrosine antibody (RC20:HRPO) was from Transduction Laboratory (Lexington, Ky.).

Cell lines and protein substrates__Human lung carcinoma cell line A549 was from ATCC. Madin-Darby canine kidney (MDCK II) epithelial cell lines and the single-chain form HGF protein were the generous gifts from Dr. George Vande Woude (NCI, NIH, Fredrick, Md.). Single-chain form of human urokinase plasminogen activator (pro-uPA) was purchased from American Diagnostic Inc (Greenwich. Conn.). Plasminnogen, plasmin, and fluorescent substrate peptides N-tert-Butoxy-Carbonyl (N-t-Boc)-Gln-Ala-Arg-7-Amido-4-Methylcoumarin (AMC), N-t-Boc-Leu-Gly-Arg-AMC, N-t-Boc-__-Benzyl (Bz)-Glu-Gly-Arg-AMC, N-t-Boc-__-Bz-Glu-Ala-Arg-AMC, N-Succinyl (Suc)-Ala-Phe-Lys-AMC, Suc-Leu-Leu-Val-Tyr-AMC, Suc-Ala-Ala-Pro-Phe-AMC, and Suc-Ala-Ala-Ala-AMC were from Sigma chemical company (St. Louis). All the other chemicals are reagent-graded.

Purification of active Matriptase__Active matriptase, in the complex form with its endogenous inhibitor HAI-1, was purified from human milk. To separate matriptase from the bound HAI-1, the complex was dissociated by acid and resolved in 10% SDS polyacryamide gel electrophoresis. The proteins were stained by Zinc stain Kit (Bio-Rad, Hercules, Calif.), the 70-kDa active matriptase was sliced out, and eluted from gel using Electro-Eluter (Bio-Rad, Hercules, Calif.) under non-denatured condition (Tris-Glysine buffer pH 8.3).

Determination of matriptase activity__The enzyme activity of matriptase was measured at room temperature in a reaction buffer containing 100 mM Tris-HCl (pH 8.5) and 100__g/ml of BSA using fluorescent peptide as substrate. In brief, 10__l of enzyme solution and 10__l of peptide substrate were added to a cuvette containing 180__l of the reaction buffer. The mixture was mixed well, placed back to a fluorescent spectrophotometer (HITACH F4500), and the release of fluorescence resulting from hydrolysis of the peptide substrate was recorded with excitation at 360 nm and emission at 480 nm.

Determination of kinetic parameter__Substrate concentration versus initial reaction velocity were analyzed by the Michaelis-Menten equation and plotted using SigmaPlot software. Double reciprocal (Lineweaver-Burk) plots thus derived were used to determine Vmax and Km values.

Cleavage of protein substrates__Single chain HGF protein, plasminogen, or pro-uPA were incubated with various amounts of matriptase in 100 mM Tris-HCl (pH8.5) overnight at room temperature. Incubation was stopped by boiling the mixture in SDS sample buffer. The cleaved products were then separated on SDS-PAGE electrophoresis and analyzed by Western blot hybridization or by silver stain.

Scattering assay__The MDCK II cell line was maintained at 37° C. in Dulbecco's Modified Eagle (DME) medium supplemented with 10% fetal calf serum (FCS). The scatter assay was carried out in the 96-well culture plate. To each well was added 150 μl DME medium supplemented with 5% FCS and leupeptin at 100 μg per ml; HGF or matriptase-cleaved HGF was added into one well and serial two-fold dilutions were made with sequential 150 ml aliquots of medium transferred from well to well. About 3,000 MDCK II cells in 150 μl medium were added to each well and the plate was placed in a 37° C. incubator for 20–24 h. Media were removed and cells were fixed and stained for 15 min with 5% crystal violet in 50% methanol. Cell scattering (spreading and dispersion of epithelial colonies) was examined under light microscopy.

Met phosphorylation detection__A549 cells were grown confluent in RPMI medium supplemented with 10% FCS. After 3-hour serum-starvation, cells were incubated 5 min incubation at 37° C. with 450 ng/ml HGF or matriptase-cleaved HGF in RPMI medium supplemented with 5% FCS. Where it is needed, leupeptin was included in the medium at 100 mg/l. Medium were removed, cells were rinsed with 1×PBS and collected by centrifugation following trypsinization. After washed one more time with 1×PBS, cell pellets were frozen in dry-ice. The frozen cell pellets were either stored at 80° C. for later extraction or immediately extracted as described below. Cells were thawed on ice, extracted by suspension in buffer containing 50 mM Tris-HCl (pH7.5), 5 mM EDTA, 150 mM sodium floride, 10 mM sodium pyrophosphate, 10 mM sodium ortovanadate, 100 mg/l PMSF, 10 mg/l leupeptine, 10 mg/l apropeptenin, and 1% Triton X-100. Extracts were clarified by centrifugation for 15 min at 12,000×g in a microfuge, and the protein concentration was determined by BCA™ protein assay kit (PIERCE, Rochford, Ill.) using bovine serum albumin (BSA) as standard. About 2 mg protein of extracts were immuoprecipitated using anti-c-Met antibody and Pansorbin (Calbiochem, La Jolla, Calif.). The protein-antibody-Pansorbin immunocomplex was collected by centrifugation, washed twice with extraction buffer then with 1×PBS, and then dissociated by boiling in SDS-sample buffer. The Pansorbin was removed by centrifugation, the supernatant fractions were subjected to 8% SDS electrophoresis, and the proteins were detected by Western immunoblot with anti-phosphotyrosin antibody. The same immunoblot were then stripped in 100 mM 2-mercaptoethonal, 2% SDS, and 62.5 mM Tris-HCl (pH7.6) for 30 min at 50° C. and re-probed with anti-c-Met antibody.

Comparison of the amino acid sequences of the protease domain of matriptase with that of other serine proteases revealed that matriptase contains a trypsin-like substrate specificity pocket, and a Asp residue positioned at the bottom of the specificity pocket. To investigate in detail the substrate specificity of matriptase, we compared the Km and Vmax of matriptase to a variety of protease substrate peptides.

Table 1. Kinetic Parameters of Matriptase for Various Peptide Substrates. 10 ml of matripase solution and 10 ml of peptide substrate were added to a cuvette containing 180 ml reaction buffer, the release of fluorescence resulting from hydrolysis of the peptide was recorded in a fluorescent spectrophotometer at room temperature with excitation at 360 nm and emission at 480 nm. Km and Vmax were determined by double reciprocal plot derived from Michaelis-Menten equation:

TABLE 1

| PeptideSubstrate | P4--P3--P2--PL-Amc | Km (uM) | $V_{max}$ (nM Amc/min) |
| --- | --- | --- | --- |
| 1 | Gln-Ala-Arg[a] | 4.887 | 654 |
| 2 | Glu-Ala-Arg | 3.808 | 76.34 |
| 3 | Leu-Gly-Arg[a] | 13.6 | 308.9 |
| 4 | Gln-Gly-Arg | 33.52 | 527.5 |
| 5 | Glu-Gly-Arg | 47.5 | 169.8 |
| 6 | Ala-Phe-Lys | 69.9 | 523.6 |
| 7 | Leu-Leu-Val-Tyr[a] | \\\\\\[b] | \\\\\\[b] |
| 8 | Ala-Ala-Pro-Phe[a] | \\\\\\[b] | \\\\\\[b] |
| 9 | Ala-Ala-Ala[a] | \\\\\\[b] | \\\\\\[b] |

[a]Gln-Ala-Arg is a standard substrate for trypsin, Leu-Gly-Arg is a substrate for uPA, Leu-Leu-Val-Tyr and Ala-Ala-Pro-Phe are the substrates for chymotrypsin, and Ala-Ala-Ala is the substrate for elase.
[b]No cleavage activity was detected with these substrates at concentration of 200 μM.

Table 1 shows that, as expected from the sequence analysis, matriptase, like trypsin, prefers to cleave peptides at Arg or Lys. Not surprisingly, the best substrate peptide for matriptase is Boc-Gln-Ala-Arg-Amc, the best substrate for trypsin. No released fluorescence was detected from the substrate for chymotrypsin or elastase (table 1, peptide substrates 7, 8, 9). Matriptase appears to prefer to bind to peptides containing small side chain amino acids, such as Ala and Gly, at P2 site (table 1, peptide substrates 1–5). Peptides containing P2 Ala are better substrates for matriptase than peptides containing P2 Gly (compare peptides 1, 2 with peptides 3–5). The binding affinity of matriptase to the formers is about 30-fold higher that to the latter. Interestingly, a change from Gln to Glu at the P3 site significant reduces the Vmax (compare peptide 1 with 2) without causing significant change on Km. Information from matriptase peptide substrate specificity led us to look for macromolcular substrates that require cleavage at Arg for activation. HGF/SF is secreted as an inactive, single chain precursor by stromal cells, and it is activated by proteolytic conversion to the two-chain form factor by cleavage at Arg-495 (19) in the extracellular environment. Furthermore, HAI1 is also the inhibitor of matriptase. HGF/SF appears to be an ideal substrate candidate for matriptase.

Figure 1B:
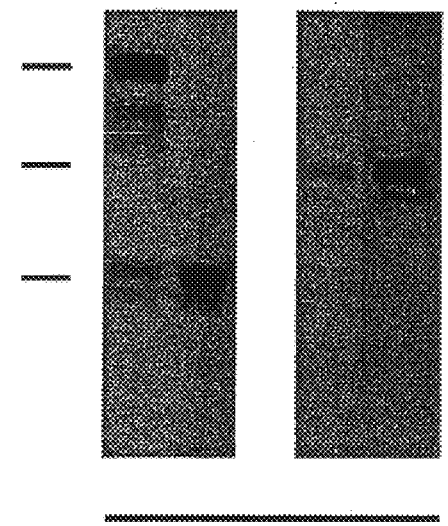

To determine if HGF/SF can be cleaved by matriptase, inactive HGF/SF purified from the condition medium of fibroblast cells cultured in the absence of serum (a generous gift from Dr. Vande Woude in NCI) was taken in the following experiments. FIG. 1A shows that this HGF/SF preparation is primarily composed of the single-chain form protein about 97 kDa on SDS-PAGE (lane a). The anti-HGF antibody apparently does not recognize the single-chain form HGF/SF (FIG. 1B).

To further investigate if the cleavage of HGF/SF by matriptase corresponds to a process of activation, we performed a well-characterized assay specific to HGF activity, the MDCK cell scatter assays. The single-chain HGF/SF was first incubated with matriptase to allow complete cleavage, the cleaved products were than diluted in the medium and incubated with MDCK II cells for 20–24 h at 37° C. To eliminate the activation of HGF/SF by other activators in the serum, leupeptin was included in every scattering assay. It was noticed that leupeptin can also inhibit matriptase enzyme activity.

Figure 2A:
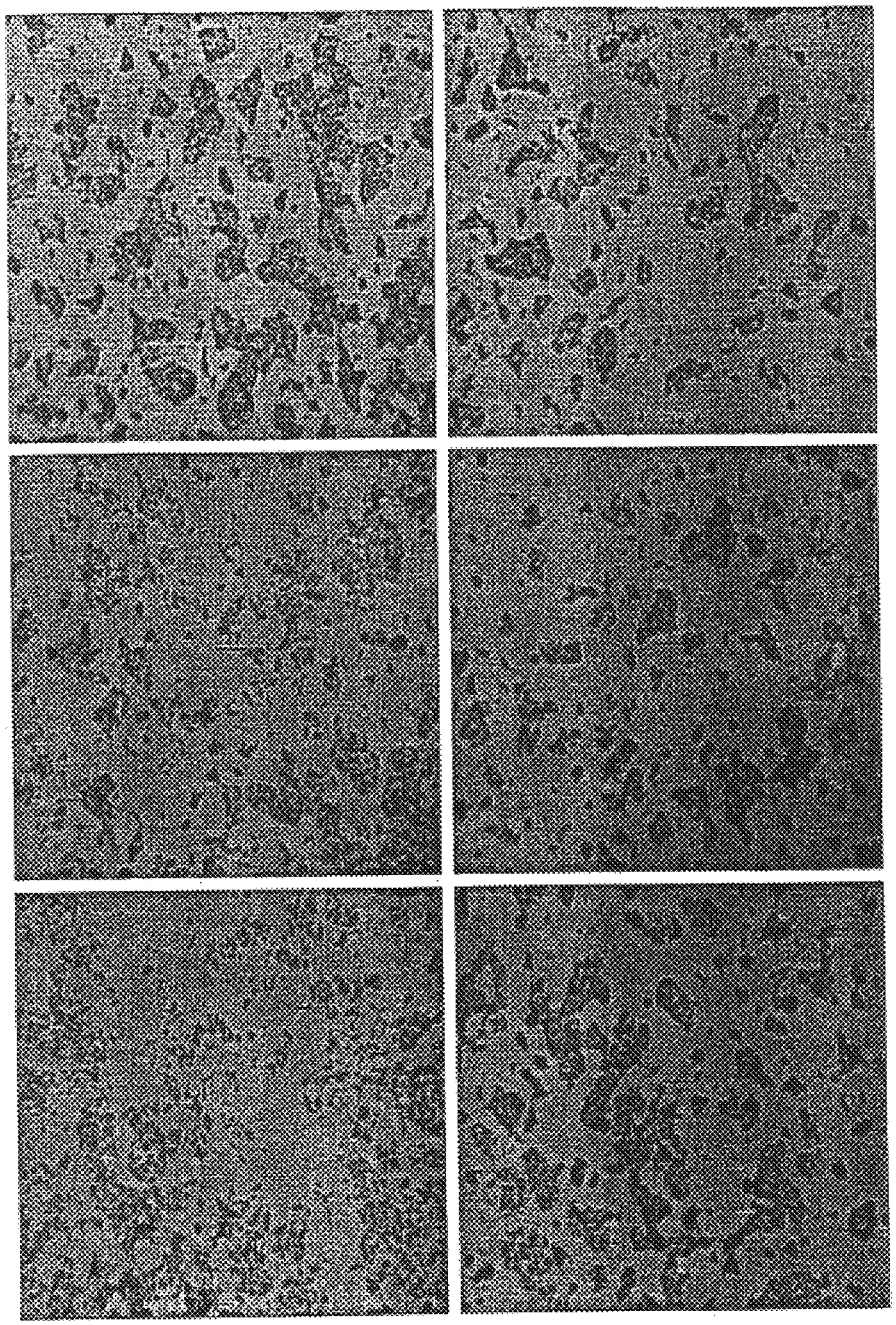
FIGS. 2A and 2B show how matriptase-cleaved HGF stimulates scattering on MDCK cells, plates show wells in the 96-well plates with about 3000 MDCK cells after 20 h in the absence (CRL) or presence of matriptase-cleaved HGF (HGF/MTP) or untreated HGF (HGF) at the dilutions shown, with leupeptin being included in every culture.
Figure 2B:
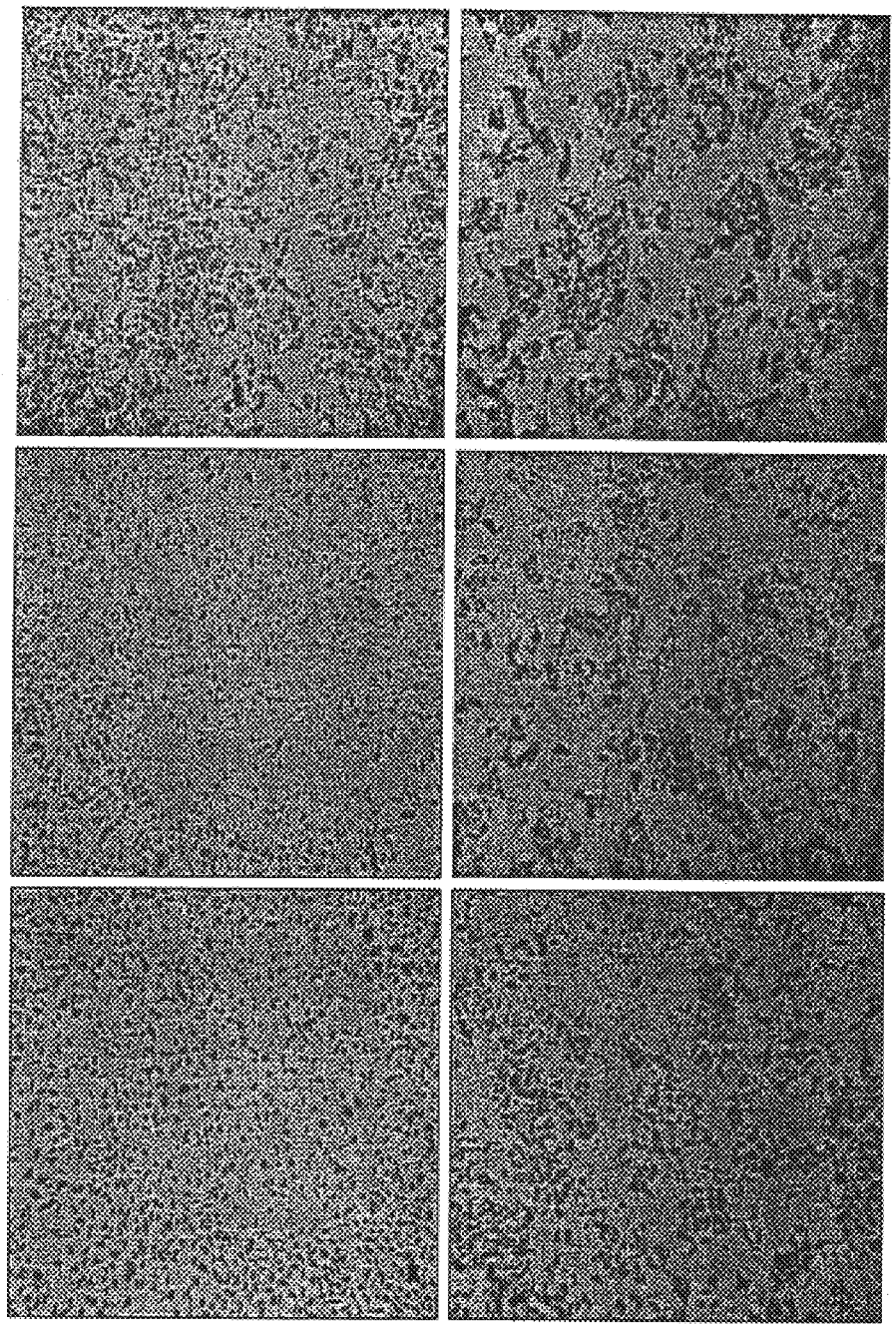

FIGS. 2A and 2B show the images of plates of MDCK II cells after incubation with various dilutions of untreated (HGF) or matriptase-treated (HGF/MTP) HGF/SF. In the control sample (CRL), cells aggregated into tight clusters after 20–24 h culture. In the presence of 1:4096 dilution of HGF/MTP, cell islands were more spread and there was a high proportion of single cells. In contrast, at the same dilution of HGF, cells were not significantly different from the control cells. The scatter morphology was more and more profound with progressively lower dilutions of HGF/MTP. At 1:512 dilution of HGF/MTP, cells completely separated from each other and many of them exhibited elongated fibroblast-like shapes. On the other hand, scattering morphology induced by the untreated HGF appeared at much lower dilution (FIGS. 2A and 2B, HGF, 1:512). The residual scattering activity in these experiments apparently come from the residual active HGF in the HGF/SF preparation (FIG. 1). Cells grown in the presence of matriptase alone retained the morphology as those in the control (data not shown). Cells incubated with untreated HGF/SF in the absence of leupeptin were examined as a positive control for HGF activation by serum; the scattering activity of HGF/SF in these samples was as expected (data not shown). These observations showed that the scattering induced by HGF/MTP is indeed contributed by the matriptase activation of HGF.

Figure 3A:
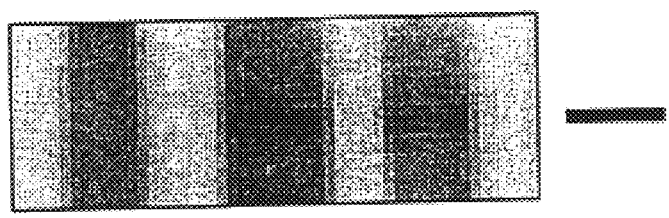
FIG. 3 shows how matriptase-cleaved HGF stimulates c-Met tyrosine phosphorylation; A549 cells were treated in the absence of HGF (NO HGF), matriptase-cleaved HGF (HGF/MTP), or HGF alone (HGF) for 5 min at 37__C; equal amounts of lysed cell protein were immunoprecipitated with anti-c-Met antibody followed by immunodetection using anti-phosphotyrosin antibody (Tyr-p) as described below; in controlling for the amounts of c-Met in each sample, immunoblots were then stripped and detected with anti-c-Met antibody (c-Met); wherein the shown arrow points to the p145 kDa__chain of c-Met under reducing conditions.
Figure 3B:
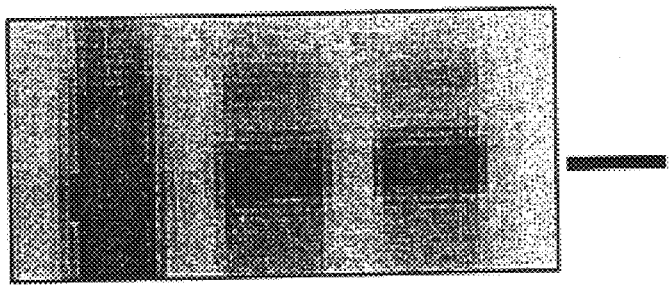

HGF operates its function through binding to its cell surface receptor, Met. Upon binding to the HGF, Met is activated following phosphorylation at tyrosine residues. In FIG. 3, c-Met activation was examined in the A549 human lung carcinoma cell line. Like the experiments for FIGS. 2A and 2B, leupeptin was also included in these treatments. Tyrosine phosphorylated c-Met was observed in the cells incubated with matriptase-cleaved HGF (HGF/MTP) and with untreated HGF (HGF), but not in the cells incubated in the absence of HGF (No HGF). Phosphotyrosine of c-Met in cells incubated with untreated HGF appears to caused by the residual active HGF contamination in the preparation. Leupeptin did not affect the total c-Met expression, the c-Met phosphorylation, or the total pattern of tyrosine phosphorylation (data not shown).

Figure 4:
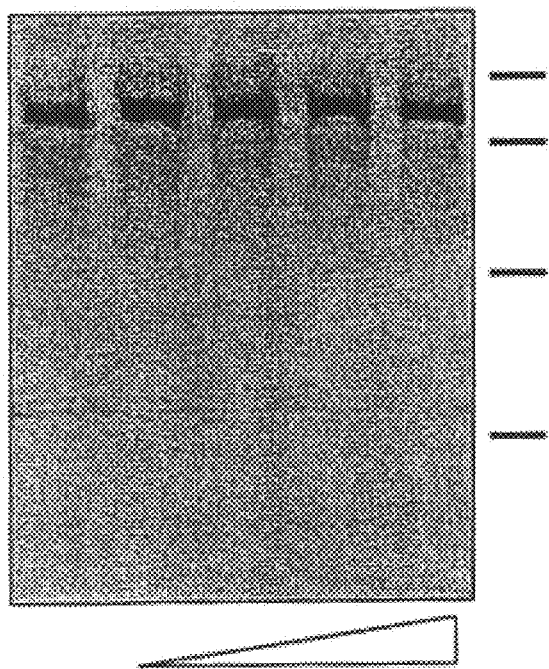
FIG. 4 shows how plasminogen is not a substrate for matriptase, this figure shows the silver-stained protein patterns of plasminogen incubated overnight without (0) or with increasing amount of matriptase ( ); with the highest amount of matritpase used is 8-fold of the lowest amount of matriptase that cleaves HGF.

Plasminogen shares high homology with HGF and its activation also requires a cleavage at Arg. It seemed likely that plasminogen would be a substrate of matriptase as well. However, to our surprise, matriptase failed to cleave plasminogen. As shown in FIG. 4, plasminogen remained as a 94 kDa single-chain form even in the presence of matriptase at 8-fold higher than that required to cleaves HGF.

Figure 5A:
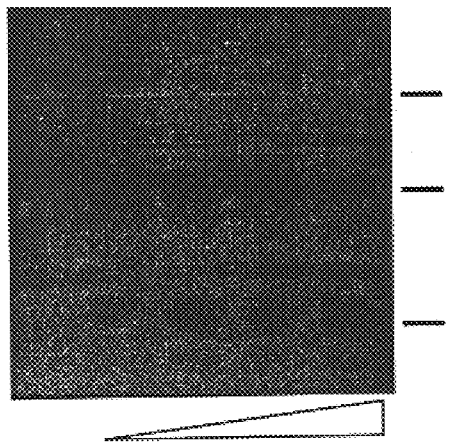
FIGS. 5A and 5B show how Pro-uPA is activated by matriptase cleavage.
Figure 5B:
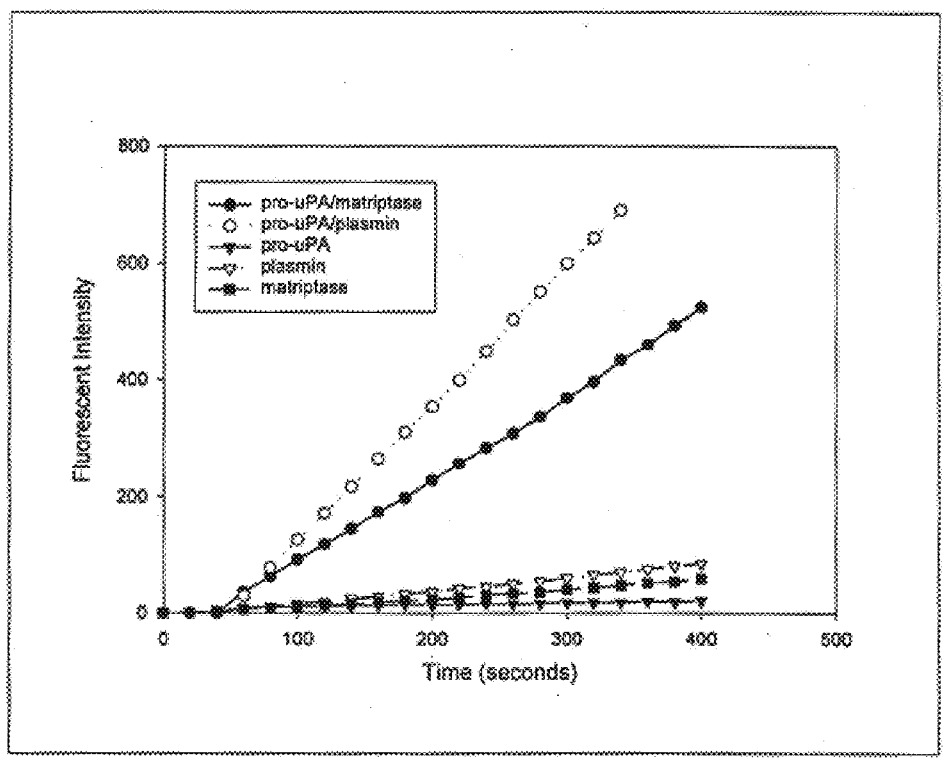

Plasmin has long been regarded as the enzyme that converts pro-uPA to active uPA. However, the level of active uPA is not reduced in the urine of mice bearing a targeted disruption of the plasminogen gene, suggesting the existence of plasmin independent pro-uPA activation. Plasma kallikrein, trypsin-like proteases from human ovarian tumors, a T cell-associated serine protease, cathepsins B and L, nerve growth factor, human mast cell trypase, and prostate specific antigenhave also been reported to activate pro-uPA. However, the roles of these enzymes in vivo, relevant to activation of pro-uPA in vivo are not clear. We were therefore interested to see if matriptase can activate pro-uPA. FIG. 5A showed that after incubation with the matriptase, the 55 kDa single-chain pro-uPA was converted into smaller fragments. One of these cleavage products clearly appeared on the protein gel as the 33 kDa molecule, which resembles the size of the active uPA protease (FIG. 5A). The cleaved product exhibited enzymatic activity toward the fluorescent peptide substrate, Boc-Leu-Gly-Arg-AMC, for uPA (FIG. 5B, compare the closed circles with closed triangles). This activity was not derived from matriptase, since matriptase alone only exhibited negligible background activity (FIG. 5B, closed squares). The same amounts of pro-uPA produced a similar activity after cleavage by plasmin (FIG. 5B, opened circles).

By using the active matriptase isolated from human milk, we report in this study that matriptase cleaves and converts HGF into a biologically functional factor that can induce c-Met activation of and stimulate epithelial cells scattering. In addition, we also noted that matriptase can activate pro-uPA but not plasminogen. These results further support matriptase to be an upstream regulator in matrix progression. Most significantly, these results reveal a novel mechanism in the control of tissue remodeling that involve an upstream epithelial membrane activator and downstream stromal effectors.

Tissue remodeling is a process observed both in physiological processes such as embryonic development, morphogenesis, and wound healing, and in pathological situations such as cancer progression and metastasis. Two essential changes occur during these processed: 1) epithelial-mensenchymal transition transforms rigid epithelial cells to the mobile menchymal cell that can migrate distances; 2) extracellular matrix degradation that open path for the migrating cells. HGF is a potent inducer of epithelial-menchymal transition; engagement of HGF to its epithelial compartment c-Met triggers various signaling subsequently induces various cellular responses. HGF is secreted as inactive precursor by stromal cells and is proteolytically activated in the extracellylar environment. Therefore, activation of HGF/SF needs to occur in the close vicinity of the epithelial cells. The network of the serine proteases uPA/uPA-receptor/plasminogen and the zinc-dependent metalloproteinases have been proposed to be responsible for the majority of proteolysis of pericellular proteins. However, both systems are largely synthesized by the stromal cells and require indirect mechanisms for their recruitment and activation on the surfaces of epithelial cells. Thus, an epithelial-derived protease like matriptase would preferably provide the missing link in this process.

In addition, the process of extracellular matrix degradation requires proteases cascades; proteolytic activation of one protease depends on the proteolytic activation of its activator. A central question in this process is that of whether there is a primary initiating enzyme. The finding that matriptase can activate both pro-uPA and HGF/SF suggesting that it should be considered as a central regulator in epithelial cell remodeling and/or progression of extracellular matix. Matriptase contains a serine protease activation motif; its activation is likely to require the proteolytic cleavage at Arg-Val. Autoactivation has been reported with the recombinant protease domain of matriptase. These observations suggest that activation of matriptase may occur intermolecularly. As we have shown previously, matriptase contains multiple non-catalytic domains that involve in protein—protein interaction. These domains may assist in accumulating other factors at the contact sites between cancer and stromal cells; these domains may also be involved in the activation of matriptase. Clues may lie in its N-terminal non-catalytic domains, particularly the CUB domains. It has been shown that CUB-EGF module in the C1r and C1s subunits play essential role in the assembly and auto-activation of the C1 complexThe same domains in matriptase may also be critical for its function. Specifically, they may contribute to an intermolecular interaction between matriptase molecules. Thus these domains may be involved in the auto-activation of matriptase, like they do in C1 complex.

Matriptase appears to have selectivity for the macromolecular substrates. In our experiments, matriptase did not cleave plasminogen, despite that the high sequence homology between plasminogen and HGF. Another group recently has also reported this substrate selectivity. In the same report, it was also showed that matriptase/MT-SP1 has selectivity for a basic residue at P3 or P4 site. The sequence at the activation cleavage site of HGF and plasminogen is P4-(Lys)-P3-(Gln)-P2-(Gly)-P1-(Arg) and P4-(Cys)-P3-(Pro)-P2-(Leu)-P1-(Arg), respectively. Thus lacking of P3 or P4 basic residue in plasminogen might attribute to its not being cleaved by matriptase. Alternatively, there might be conformational differences between HGF and plasminogen. The kringle domains of plasminogen contain a Lys-binding site that serves to mediate its localization to fibrin and to cellular surfaces. Plasminogen circulates in the blood in a globular and closed conformation; upon binding to the surface, it shifts to an extended and opened conformation. This conformation change promotes its recognition by its activator and its rapid convert to plasmin. The kringle domains on HGF/SF also contribute to its binding to its receptor c-Met. However, cleavage-activation of HGF/SF does not depend on its binding to c-Met. It is possible that the single chain form HGF/SF exhibit a more open conformation than does plasminogen; and that matriptase can distinguish this subtle structural difference.

Identification of Small Molecules Capable of Inhibiting Matriptase Action

As disclosed supra, the focus of the subject invention is to provide therapies based on compounds capable of interfering with matriptase protease activity. In one aspect, the invention provides therapies based on existing compounds which are identified through computational modeling as inhibitors of matriptase activity. The compounds are identified through structure-based three-dimensional (3D) database searching. The compounds identified through database searching are processed through biological tests to identify one or more lead compounds for clinical testing and/or rational drug design refinement.

Computationally predicting a compound's binding affinity to a host protein involves utilizing the three dimensional (3-D) structures of the host protein and the compound. The 3-D structure of the compound is obtained from a database of chemical compounds. The 3-D structure of the host protein can also be obtained from a protein database.

The invention provides potent and specific matriptase inhibitors through a structure-based drug discovery approach. The methodology employed in the discovery of matriptase inhibitors is disclosed in U.S. patent application Ser. No. 09/301,339, filed on Apr. 29, 1999, the contents of which are hereby incorporated by reference in their entirety.

Briefly, in structure-based 3D-database searching for drug discovery, once the 3D structure of the target molecule (a receptor or an enzyme) is determined, large chemical databases containing the 3D structures of hundreds of thousands of structurally diverse synthetic compounds and natural products are searched through computerized molecular docking to identify small molecules that can interact effectively with the target or host molecule.

In spite of the massive increase in the number of biological molecules whose 3-D structure has been elucidated, the majority of proteins of known primary structure (amino acid sequence) do not have a known tertiary (or 3-D) structure.

For drug design involving target proteins of unknown tertiary structure, a model structure can be constructed based on the known tertiary structure of a protein which is homologous to the target protein. The structure of the homologous protein is used to construct a template structure of all or part of the target protein. The structure obtained through homology modeling provides a working structure for further refinement. The working structure for the protein not having a known structure is obtained by refining the template structure.

In forming a template 3-D structure of the host protein, each atom of the backbone of the target protein is assigned a position corresponding to the position of the equivalent backbone atom in the homologous protein. Similarly, each atom of a side chain of the target protein having an equivalent side chain in the homologous protein is assigned the position corresponding to the position of the atom in the equivalent side chain of the homologous protein. The atom positions of a side chain not having an equivalent in the homologous protein are determined by constructing the side chain according to preferred internal coordinates and attaching the side chain to the backbone of the host protein.

The template structure thus obtained is refined by minimizing the internal energy of the template protein. During the refinement, the positions of the atoms of the side chains having no equivalents in the homologous protein are adjusted while keeping the rest of the atoms of the template protein in a fixed position. This allows the atoms of the constructed side chains to adapt their positions to the part of the template structure determined by homology. The full template structure is then minimized (relaxed) by allowing all the atoms to move. Relaxing the template 3-D structure of the protein eliminates unfavorable contacts between the atoms of the protein and reduces the strain in the template 3-D structure.

Based on the refined structure of the target protein, a host-guest complex is formed by disposing a compound from a compound database in a receptor site of the protein. The structure of the host-guest complex is defined by the position occupied by each atom in the complex in a three dimensional referential.

A geometry-fit group is formed by selecting the compounds which can be disposed in the target binding site without significant unfavorable overlap with the atoms of the protein. For each compound in the geometry fit group, a predicted binding affinity to the receptor site of the host protein is determined by minimizing an energy function describing the interactions between the atoms of the compound and those of the protein. The minimization of the energy function is conducted by changing the position of the compound such that a guest-host complex structure corresponding to a minimum of the energy function is obtained. The compounds having the most favorable energy interaction with the atoms of the binding site are identified for optional further processing, for example through display and visual inspection of compound protein complexes to identify the most promising compound candidates.

The displayed complexes are visually examined to form a group of candidate compounds for in vitro testing. For example, the complexes are inspected for visual determination of the quality of docking of the compound into the receptor site of the protein. Visual inspection provides an effective basis for identifying compounds for in vitro testing.

After putative binding compounds have been identified, the ability of such compounds to specifically bind to matriptase is confirmed in vitro and/or in vivo.

Potent and selective inhibitors are tested further in their ability to inhibit colony-formation in soft-agarose. Compounds having good in vitro activity are tested in vivo. Tumor bearing mice are treated with therapy, based on the compounds and the effect on the tumor size is observed. Compounds showing effective tumor reduction are then used in clinical trial protocols.

Figure 6:
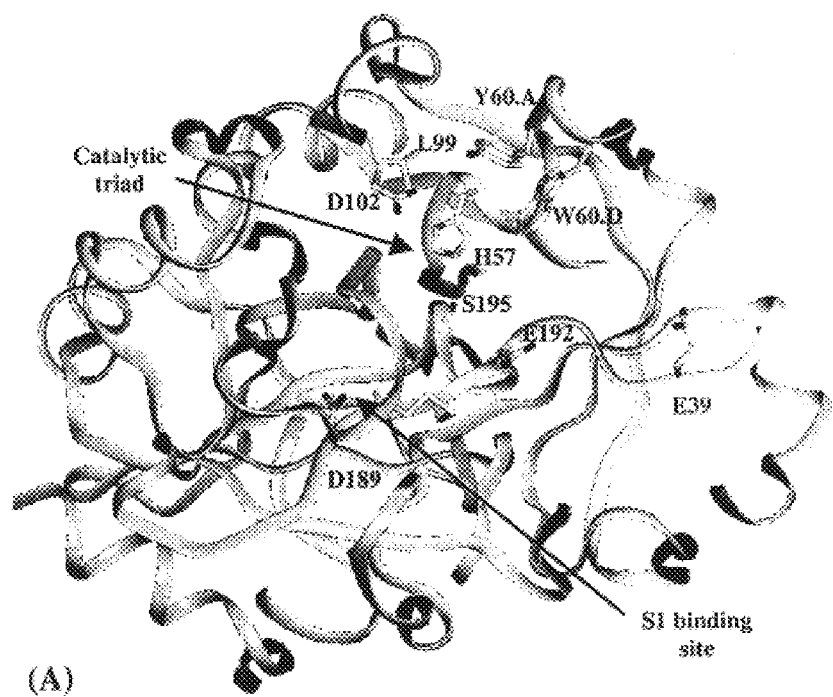
FIG. 6A. shows the active-site residues in thrombin, entry 1HXE in the protein databank.
FIG. 6B shows the active site of matriptase, as obtained after homology modeling and refinement using molecular dynamics simulation in water.
Figure 6:
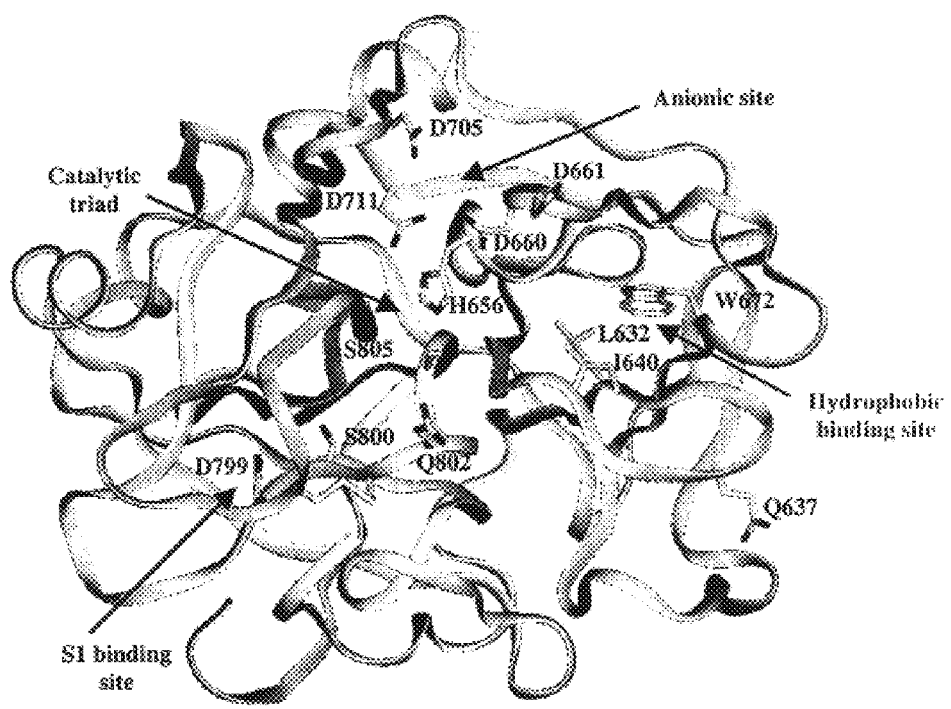

Computational Identification of Compounds Having Potential Matriptase Inhibitory Activity Homology Modeling. The X-ray structure of human thrombin, entry 1hxe (FIG. 6A) from the protein databank[14], was used as template for building the 3D structure of the protease domain of matriptase using homology modeling. It was shown that when the sequence identity/similarity between the modeled protein and the template is between 30% and 40% the expected main-chain RMS error of the model compared to the real structure is about 1.5 Å for 80% of residues[15, 16]. Since the sequence identity and similarity between thrombin and matriptase are 34% and 53%, respectively and both enzymes belong to the same protease family, we can model the structure of matriptase accurately. FIG. 6B shows the modeled structure of the protease domain of matriptase. By analogy to thrombin the serine protease domain of matriptase has a catalytic triad, formed by Ser805, His656, and Asp711 and positioned on the surface of the protease domain. This corresponds to Ser195, His57 and Asp102 in Thrombin. Consistent with the observation that matriptase prefers substrates with an Arg or Lys as P1 residue[10, 12], a negatively charged residue, Asp799, is located at the bottom of the S1 binding site. This residue corresponds to Asp189 in thrombin. S1 site residue Ser800 from matriptase corresponds to Ala190 from thrombin. An anionic site formed by Asp660, Asp661, and Asp705 may also be important for inhibitor binding to matriptase. Close to the S1 site Gln802 and Gln637 in matriptase correspond to charged Glu192 and Glu39, respectively in thrombin. Anionic site residues Asp705, Asp660 and Asp661 from matriptase correspond to Trp96, Tyr60.A and Trp60.D, respectively in thrombin. This shows that this site in matriptase is charged while it is neutral in thrombin. A putative hydrophobic S1' binding site is marked by Leu632, Ile640, and Trp672, as shown in FIG. 1B, that is similar to Leu33, Leu41 and Leu64 in thrombin, FIG. 6A.

The sequence for matriptase was obtained from sequencing data. Templates for homology modeling were obtained by searching the Protein Databank[14], using the program BLAST.[21] The structure of thrombin, entry 1HXE with 34% identities, 53% similarity and 6% gaps, was used as a template for modeling matriptase structure using the program MODELLER.[15] The structure obtained from homology modeling was further refined using the molecular dynamics program CHARMM.[22]. Hydrogen atoms were assigned to the modeled structure using the program HBUILD[23] from CHARMM. The protein was then solvated by inserting it in a 30 Å sphere of water and by deleting solvent molecules with heavy atoms that are at less than 2.5 Å from protein heavy atoms. The MD simulation was done using the all atom parameter set from QUANTA force field, a constant dielectric, $\in=1$ and constant temperature, T=300 K. The leap frog method with 1 fs time step was applied for numerical integration. Long-range electrostatic forces were treated with the force switch method in a switching range of 8–12 Å. Van der Waals forces were calculated with the shift method and a cutoff of 12 Å. The nonbond list was kept to 14 Å and updated heuristically. Solvent waters were kept from evaporating by using a spherical miscellaneous mean field potential as implemented in CHARMM. The solvated protein was energy minimized using 250 cycles of Steepest Descent and 500 cycles of Adopted-Basis Newton Raphson methods. This was followed by 100 ps molecular dynamics simulation.

The structure of thrombin, entry 1HXE from the protein databank, was prepared for docking in the same way as the structure of matriptase.

Structure-Based 3D Database Screening.

The refined structure of matriptase obtained from homology modeling, as described in the previous section, was used as the target in a structure-based 3D database search. The program DOCK[24] was used for computer-aided database screening to identify potential inhibitors. Shape and binding energy scoring functions were used to screen and rank the potential ligands. Filters were used to eliminate molecules that have more than 10 flexible bonds, in order to avoid considering overly flexible molecules; were also discarded molecules with fewer than 10 or more than 50 heavy atoms.

The screening of the large NCI database was done on a Silicon Graphics Indigo2 R10000 workstation. The docking was done in two stages, with the ligand flexibility being considered in both. In the first stage, two minimization cycles, with 50 iterations maximum, were considered for each compound from the database. The best-scoring 10,000 molecules were considered in the second stage, when 100 minimization cycles and 100 maximum iterations per cycle were carried out in order to refine the position of the ligand and its score. The top 2,000 compounds were then considered for selecting potential inhibitors for matriptase by inspection to determine if they contain ionizable groups that will bind to the S1 site and the anionic site. After these screening, 69 compounds were selected for further biochemical testing.

The refined structure of matriptase, obtained from molecular dynamics simulation, was used for structure-based screening of the NCI database. Since the S1 site is considered to be the primary binding site in serine proteases, it is likely to be a good target site for inhibitor design[6; 17]. In addition, other two putative binding sites, the anionic site and the hydrophobic S1', were included in the docking site used for 3D-database searching with the program DOCK[18]. Ligands were scored based on the DOCK energy score computed as a sum of the electrostatic, van der Waals and ligand conformational energy. Since the primary binding site of matriptase is negatively charged, the potential inhibitor candidates that target this site should be positively charged in solution. Using this idea a total of 69 candidate compounds were selected for testing from the best scoring 2,000 compounds based upon the DOCK program.

Inhibitory Activity Screening.

Materials. Active matriptase was purified from human milk as will be described later. Active urokinase-type plasminogen activator (uPA) was purified by aminobenzamidine-Sepharose 6B (Amersham Pharmacia, Piscataway, N.J.) from a partially purified uPA from human urine. Bovin β-trypsin, bovine thrombin, and fluorescent peptide substrates N-tert-Butoxy-Carbonyl (N-t-Boc)-Gln-Ala-Arg-7-Amido-4-Methylcoumarin (AMC), N-t-Boc-Leu-Gly-Arg-AMC, and N-t-Boc-Leu-Arg-Arg-AMC were purchased from Sigma (Sigma Chemical Company, St. Louis). Small molecule inhibitors were obtained from the Drug Synthesis & Chemistry Branch, Developmental Therapeutics Program, Division of Cancer Treatment and Diagnosis, National Cancer Institute. Other chemicals are all reagent grade.

Purification of Active Form Matriptase. Activated matriptase, in a complex with its endogenous inhibitor HAI-1, was purified from human milk by immunoaffinity chromatography, and maintained in its uncomplexed status in glycine buffer pH 2.4, as described previously[11]. Matritpase and HAI-1 were further separated by 10% SDS polyacryamide gel electrophoresis. The proteins were stained by Zinc stain Kit (Bio-Rad, Hercules, Calif.). Gels containing the 70-kDa active matriptase was sliced out, and eluted from gel using Electro-Eluter (Bio-Rad, Hercules, Calif.) under non-denatured conditions (Tris-Glysine buffer pH 8.3). Purified, active matriptase was then stored at –80° C. in acid solution.

Determination of Inhibitory Activity. Inhibitory activity of compounds against each protease was measured at room temperature using fluorescent substrate peptides in 100 mM Tris-HCl (pH 8.5), containing 100 µg/ml of bovine serum albumin. To a cuvette containing 170 µl buffer was added 10 µl of enzyme solution and 10 µl of inhibitors. After pre-incubation, 10 µl of substrate was added, and the solution was mixed well by shaking the cuvette. The residual enzyme activity was then determined by following the change of fluorescence released by hydrolysis of the fluorescent substrates in a fluorescent spectrophotometer (HITACHI F4500), with excitation at 360 nm and emission at 480 nm. Peptide N-t-Boc-Gln-Ala-Arg-AMC was used as a substrate for matriptase and trypsin, peptide N-t-Boc-Leu-Gly-Arg-AMC was used as a substrate for uPA, and peptide N-t-Boc-Leu-Arg-Arg-AMC was used as a substrate for thrombin.

Kinetic Screening of Compound Inhibitors. The inhibitory activity of each compound was first investigated by using a fixed (75 µM) concentration both of inhibitor and matriptase. Compounds that exhibited inhibition were then subjected to a further analysis for their $K_i$ values using Dixon plotting. We recorded the rate of hydrolysis in duplicate in the presence of 6–7 different concentrations of each inhibitor. A straight line of the concentration of inhibitor versus the reciprocal values of the rate of hydrolysis was plotted with SigmaPlot software. Two lines were obtained from two unsaturated substrate concentrations; the X value of the intersection of these lines gives the value of $-K_i$.

TABLE 2

Initial screening of compound inhibitors for matriptase.

| Behavior | Numbers of Compound |
| --- | --- |
| over 95% inhibition | 15 |
| 90% to 94% inhibition | 4 |
| 70% to 89% inhibition | 15 |
| 40% to 69% inhibition | 13 |

TABLE 2-continued

Initial screening of compound inhibitors for matriptase.

| Behavior | Numbers of Compound |
| --- | --- |
| below 39% inhibition | 17 |
| High Absorbency | 3 |
| Increase activity | 3 |

Table 2 shows the results from an initial inhibitory activity screening. Each of the 69 candidate compounds was tested at 75 μM for the inhibitory activity against matriptase. 47 compounds inhibited at least 40% of the protease activity and 15 of them inhibited more than 95% of the protease activity. There were 6 compounds found not to be useful in the screening assay: 3 compounds had high absorbency which made them incompatible with the screening assay; three other compounds increased, rather than reduced, the rate of fluorescence release following hydrolysis by matriptase. The 15 compounds that exhibited more than 95% inhibition were analyzed further for their $K_i$ values, as described in experimental section.

TABLE 3

$K_i$ values obtained for bis-benzamidine analogs of hexamidine.

| Cpd | Structure | $K_i$ (nM) | | |
| --- | --- | --- | --- | --- |
| | | Matriptase | UPA | Thrombin |
| 1 | 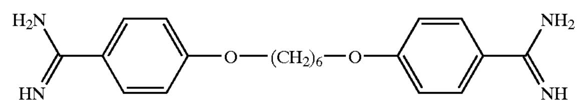 | 924 | 14,400 | 224 |
| 2 | 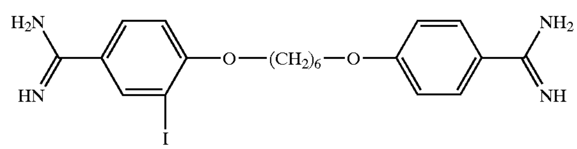 | 191 | 1,980 | 796 |
| 3 | 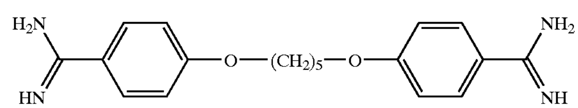 | 1,160 | | |
| 4 | 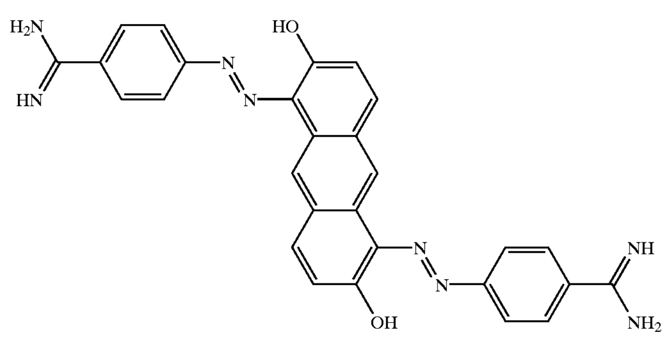 | 4,500 | 28,400 | |
| 5 | 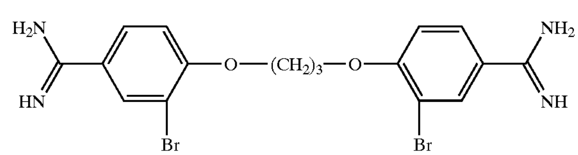 | 535 | 1,570 | 946 |
| 6 | 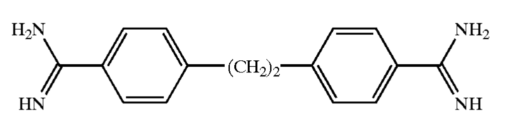 | >10,000 | | |

TABLE 3-continued

$K_i$ values obtained for bis-benzamidine analogs of hexamidine.

| Cpd | Structure | $K_i$ (nM) Matriptase | UPA | Thrombin |
|---|---|---|---|---|
| 7 | H₂N-C(=NH)-C₆H₄-O-C₆H₄-O-C₆H₄-C(=NH)-NH₂ | 208 | 1,950 | 2,670 |

Bis-Benzamidines as a Class of Potent Matriptase Inhibitors. One of the compounds that we have identified from screening is hexamidine, compound 1, a

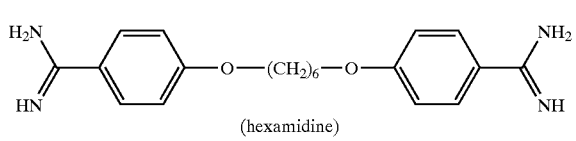

(hexamidine)

topical antiseptic. It inhibits matriptase with a $K_i$ of 924 nM, which makes it a good lead compound for further optimization. We therefore tested its closely related analogs that are available from the NCI database. This approach can lead to the discovery of more potent and more selective compounds. We tested 7 bis-benzamidine analogs of 1 that are available in the NCI database. Their chemical structures and their $K_i$ values in inhibition of matriptase enzymatic activity are summarized in Table 3. The $K_i$ values of these compounds ranged from 191 nM to greater than 10 μM. Dixon plots of these inhibitors behaved like competitive inhibitors to the peptide substrate.

Compounds 1, 2, 5 and 7, with $K_i$ value below 1 μM, were further evaluated for their selectivity against two other serine proteases: uPA and thrombin. Thrombin is a serine protease that plays a role in blood clotting and its structure was used as the template to model the structure of matriptase. uPA is another serine protease, which was proposed to play a role in cancer invasion and has a high sequence homology to matriptase[4].

Compound 1 is 16-fold less potent as an inhibitor for uPA than for matriptase. However, compound 1 is a more potent inhibitor for thrombin ($K_i$=224 nM) than for matriptase. Both 1 and 2 have a linker with the same length, but 2 has a 3-iodo substituent on one benzamidine phenyl ring. This iodo substituent improved the potency for matriptase by approximately 5-fold, while decreased the potency for thrombin by approximately 4-fold. Thus, compound 2 is more selective for matriptase versus thrombin. This suggests that substituents on the benzamidine phenyl ring can improve the potency and selectivity of bis-benzamidines for matriptase. A structural comparison of compounds 1, 3, and 6 shows that the length of the linker between the two benzamidine groups is important for the inhibitory activity of bis-benzamidines. As the length of the linker decreases, the potency of the inhibitors decreases. Based upon our modeled matriptase structure, the distance between the S1 binding site and the anionic binding site is approximately 21 Å, similar to the length of 1 and 3 when they adopt a fully extended conformation. Although compound 5 has a shorter linker than do 1 and 3, it is approximately 2-fold more potent than 1 and 3 against matriptase. This suggests that 3,3'-dibromo substituents on the benzamidine phenyl rings can also improve the inhibitory potency of a compound. Compound 7 is one of the most rigid compound among the potent inhibitors tested in this study. Despite that compound 7 has a shorter linker than 2 does, 7 is as potent inhibitor as compound 2 against matriptase. Furthermore, 7 has improved selectivity between matriptase and thrombin as compared to 2 and is the most selective inhibitor for matriptase among all the compounds tested. The conformational rigidity of 7 may play a role for its good potency and improved selectivity.

Figure 7:
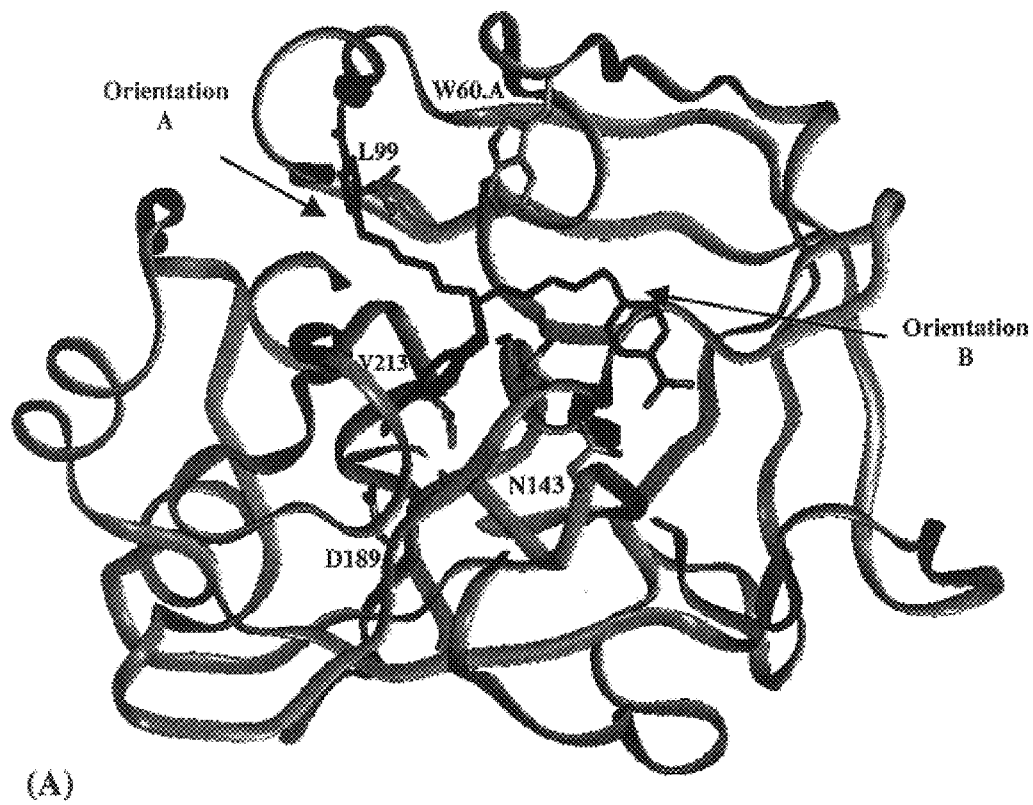
FIG. 7A. shows different starting orientations of 1 in the active site of thrombin obtained after flexible ligand docking with the program DOCK.
FIG. 7B. shows orientation of 1 in the active site of matriptase obtained after flexible ligand docking with DOCK
Figure 7:
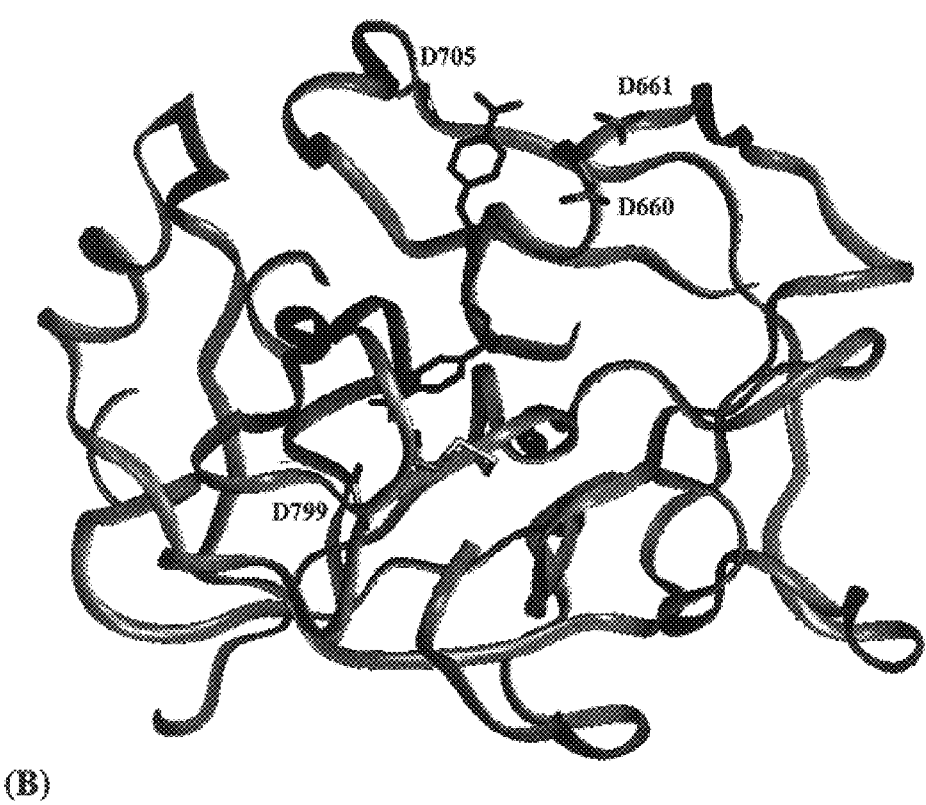
Figure 8:
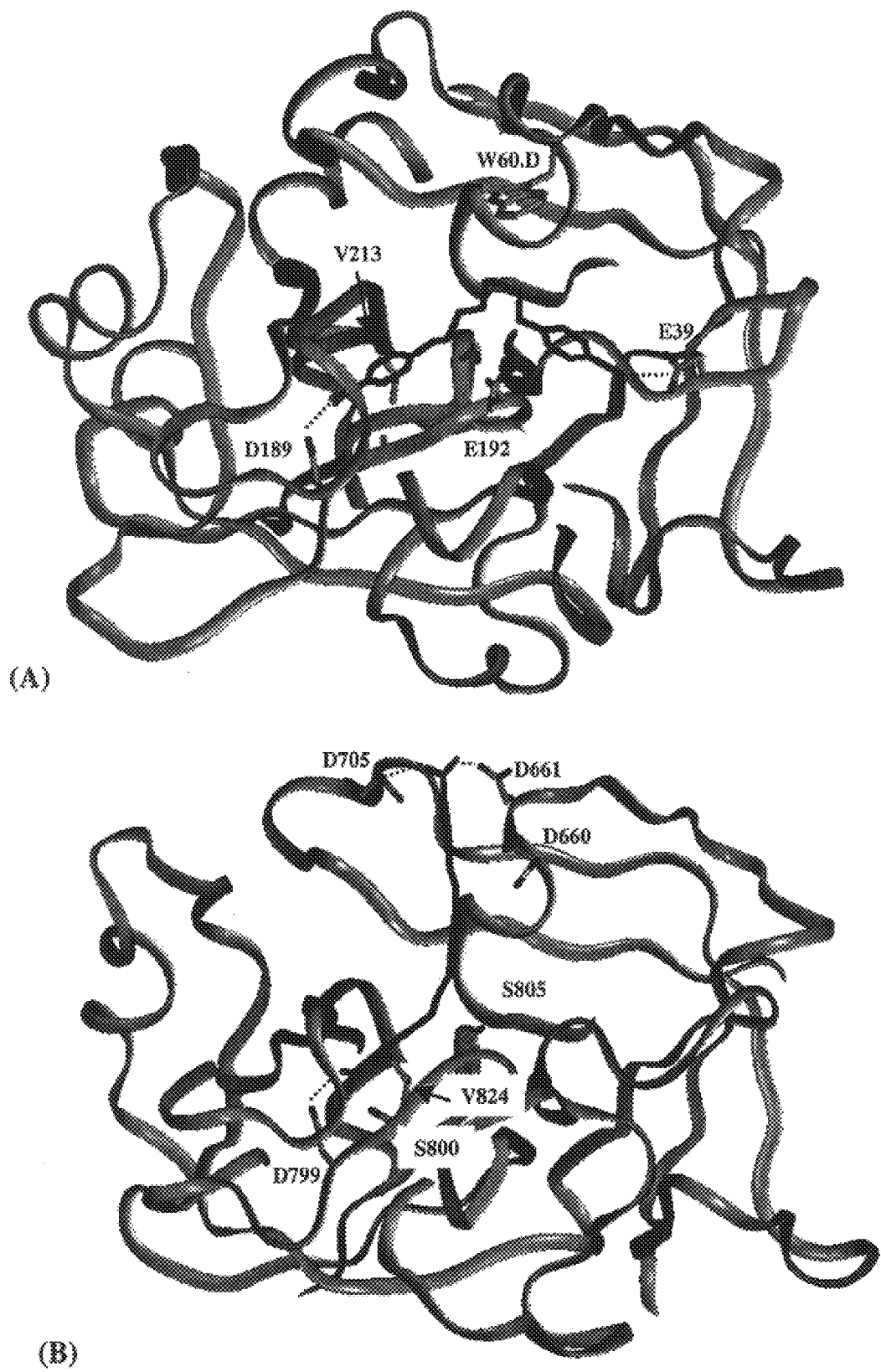
FIG. 8 shows the lowest energy structure of the complex of compound 1 with A. thrombin and B. matriptase obtained after refinement using molecular dynamics simulation with the generalized effective potential.
Figure 9:
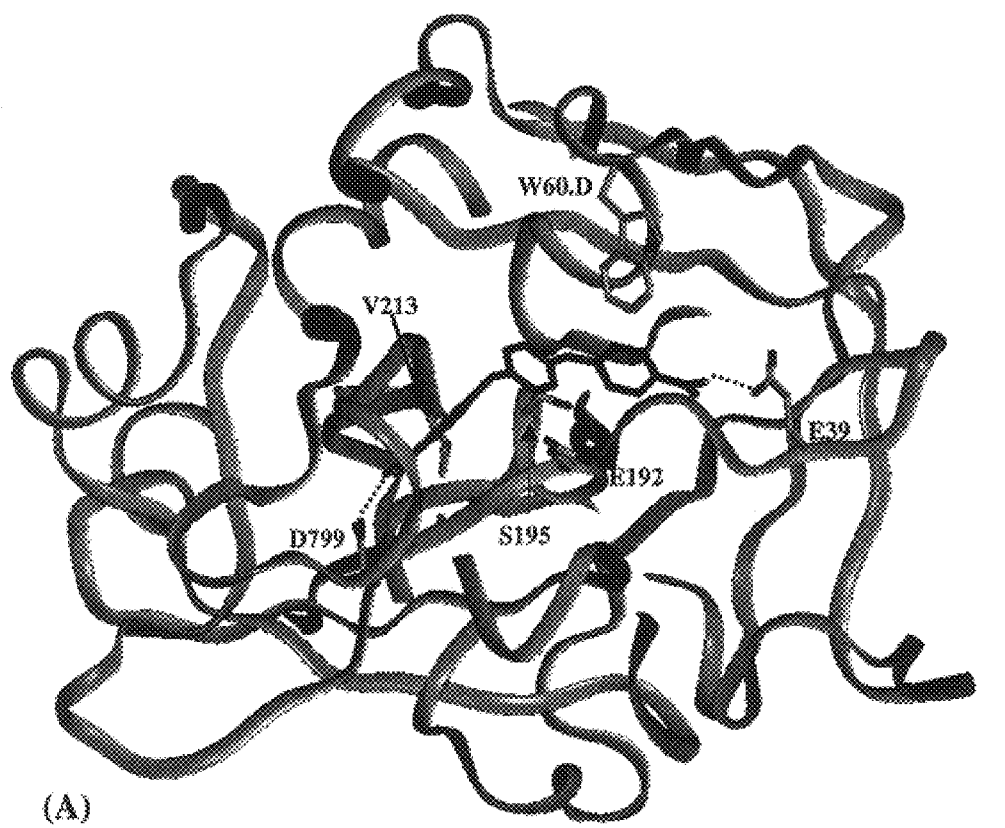
FIG. 9 shows the lowest energy structure of the complex of compound 7 with A. thrombin and B. matriptase obtained after refinement using molecular dynamics simulation with the generalized effective potential.
Figure 9:
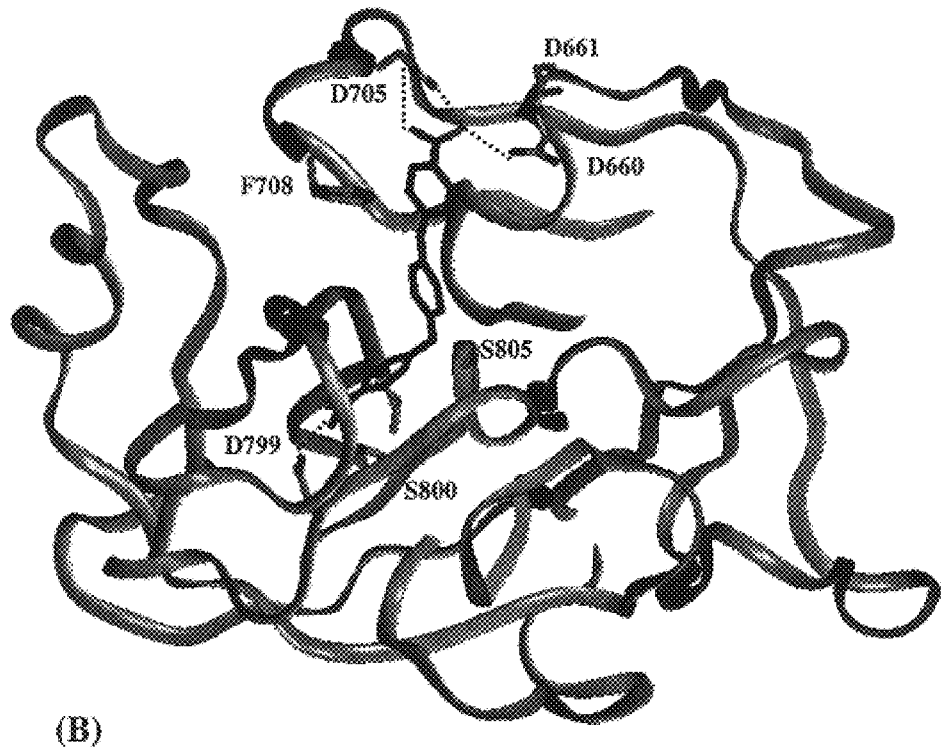

Docking Results. To gain a better understanding of the interactions between bis-benzamidines and matriptase or thrombin we have docked compounds 1 and 7, with $K_i$ less than 1 μM, into the active site of both proteins. The goal of this study is to understand why compound 1 is thrombin selective while 7 is matriptase selective. Building the inhibitor-protein complexes was done in two steps. First every compound was docked into the corresponding protein using DOCK. During this docking the ligand was flexible while the protein structure was rigid. To take in account the flexibility of the protein, the complex structure was further optimized using molecular dynamics simulation with a generalized effective potential[19] followed by regular molecular dynamics simulation. Docking with DOCK of 1 and 7 lead to two different possible binding modes of each ligand to thrombin. As shown in FIG. 7A. each ligand can adopt two different orientations. The first one, A, in which the second benzamidine fragment interacts with main-chain carbonyl oxygens in a region that corresponds to the anionic site in matriptase, FIG. 7A. In the second orientation, B, the second benzamidine fragment of the inhibitor interacts with Asn143 or Glu192, depending on the length of the linker, FIG. 7B. In order to decide which orientation is the more favored one we did two parallel simulations for compound 1 using molecular dynamics with the effective generalized potential. After 1 ns both simulations predicted the same the binding mode of 1 in which it forms salt bridges with both Asp189 and Glu39 from thrombin, FIG. 8A. This shows that considering the flexibility of the receptor in docking studies is very important. Starting from orientation A, FIG. 7A, simulation of thrombin complex with 7 led to a similar binding mode as obtained for 1. Based on our simulation results both inhibitors interact with the S1 site through salt bridge to Asp189, hydrophobic interaction with Val213 and weak hydrogen-bond between the amidino group of the inhibitor and the carbonyl oxygen of Ala190, FIG. 8A and FIG. 9A. Compound 1 interacts with Trp60.D through its linker, FIG. 8A, and 7 interacts through the second benzamidine fragment, FIG. 9A. Compound 1 forms bidentate hydrogen-bonding interaction with the carboxylate of Glu39, while 7 forms monodentate hydrogen-bonding interactions with the carboxylate of Glu39. The rigid linker in 7 does not allow a favorable orientation of the amidino group to form a bidentate hydrogen-bonding interaction with Glu39. Bidentate hydrogen-bonding interactions between oppositely charged groups are known to be more stable than monodentate interactions as observed for a series of thrombin inhibitors[20] which may be one of the reasons why 7 is less potent than 1.

Molecular Modeling of the Best Scoring Ligands. Compounds with $K_i$ less than 1 $\mu$M against matriptase were also docked into thrombin using DOCK with the second protocol as shown above. The orientation of the ligand obtained after docking was used as starting orientation in molecular dynamics refinement, that was done on a Beowulf cluster of PCs in our laboratory. The active site of the protein-inhibitor complex was solvated by centering the molecule on Ser805/Ser195. A 20 Å radius TIP3P[25] water sphere centered in the origin was then added for solvation. Water molecules closer than 2.5 Å to any protein or inhibitor heavy atom were deleted. The solvated structure was minimized using the same protocol as described before. The solvated complex was energy minimized using 250 cycles of Steepest Descent and 500 cycles of Adopted-Basis Newton Raphson methods. This was followed by 1 ns MD refinement using the generalized effective potential implemented in CHARMM by our group[19]. The temperature of the simulation was 300 K and a 1 fs time step was used for numerical integration of the equation of motion. Long-range electrostatic forces were treated with the force switch method in a switching range of 8–12 Å. Van der Waals forces were calculated with the shift method and a cutoff of 12 Å. The nonbond list was kept to 14 Å and updated heuristically. For ligand optimization an annealing protocol was used with the maximum q value[19] for calculating the generalized effective potential of 1.0005, this value was reached after 10 ps simulation, followed by 10 ps simulation during which the q value was decreased to 1, that corresponds to MD, and 30 ps MD simulation. This cycle was repeated for the entire length of the simulation. A harmonic restraining force, with a force constant of 0.5 kcal/Å$^2$, was applied on the protein main-chain atoms that are within 20 Å of the catalytic triad Ser805/195. Residues that were farther than 20 Å from the active site Ser were fixed. This was followed by 1 ns regular molecular dynamics simulation at 300 K without restraining force on the protein main-chain atoms. During this simulation residues that were farther than 20 Å from the catalytic triad Ser were also fixed. We used the same setup as for the generalized effective potential with the exception that q was 1 during the entire length of the simulation.

Docking of 1 and 7 into matriptase using the program DOCK resulted in only one favored orientation of the inhibitors, FIG. 7B. All molecular dynamics simulations were done using the starting orientation of the ligand as predicted by docking. Based on our simulation of matriptase-inhibitor complexes, we propose that 1 and 7 interact with the S1 site of matriptase through salt bridge with Asp799, hydrogen bond with Ser800 OH and hydrophobic interaction with Val 824, FIG. 3B and FIG. 4B. These interactions are similar to those found in thrombin. However, 1 forms two monodentate hydrogen-bonding interactions with Asp705 and Asp661 in matriptase that correspond to a bidentate hydrogen-bonding interaction with Glu39 in thrombin. Also the linker of 1 does not form hydrophobic interactions with matriptase as opposed to thrombin, which may be one explanation for the selectivity of this inhibitor for thrombin. The shorter 7 forms bidentate hydrogen-bonding interaction with Asp705 and a monodentate hydrogen-bonding interaction with Asp660, which is a stronger interaction than the one observed in thrombin, FIG. 9A. This may explain the stronger binding of 7 to matriptase than to thrombin. In addition the last benzamidine fragment forms hydrophobic interactions with Phe708 that are similar to those observed in thrombin.

Thus, the present invention provides bis-benzamidines as a class of matriptase inhibitors through structure-based database search. The lead compound, hexamidine (1) has a $K_i$ value of 924 nM in inhibiting of matriptase. Testing available analogs of the lead compound (1) led to the identification of 2 and 7 that are better inhibitors of matriptase with $K_i$ values of 191 and 208 nM, respectively. Compound 7 is the most selective compound among the compounds tested. It has a selectivity of 9-fold and 13-fold between matriptase and uPA, and between matriptase and thrombin, respectively. Our limited structure-activity relationship and docking studies showed that the length of linker between the two benzamidine groups, the conformational rigidity of the linker, as well as the substituent(s) on the benzamidine ring(s) play important roles for the activity and selectivity. Differences in the relative position to the S1 site of the anionic site in matriptase versus thrombin can be used to design matriptase selective inhibitors. The discovery of these small molecule and non-peptide matriptase inhibitors provides us with valuable pharmacological tools to further elucidate the biological function of matriptase. Structure-based design and chemical modifications toward improving potency and selectivity discovered lead compounds are currently under way and will be reported in due course.

Thus, the compounds produced according to the invention will be used to treat conditions wherein inhibition of matriptase is therapeutically beneficial. This will include conditions that involve abnormal cell growth and/or differentiation such as cancers and other neoplastic conditions. Examples of cancers which may be treated according to the invention include colon, pancreatic, prostate, head and neck, gastric, renal, brain and CML.

The subject therapies will comprise administration of at least one compound according to the invention in an amount sufficient to elicit a therapeutic response, e.g., inhibition of carcinoma progression.

The compound may be administered by any pharmaceutically acceptable means, by either systemic or local administration. Suitable modes of administration include oral, dermal, e.g., via transdermal patch, inhalation, via infusion, intranasal, rectal, vaginal, topical parenteral (e.g., via intraperitoneal, intravenous, intramuscular, subcutaneous, injection).

Typically, oral administration or administration via injection is preferred. The subject compounds may be administered in a single dosage or chronically dependent upon the particular disease, condition of patient, toxicity of compound, and whether this compound is being utilized alone or in combination with other therapies. Chronic or repeated administration will likely be preferred based on other chemotherapies.

The subject compounds will be administered in a pharmaceutically acceptable formulation or composition. Examples of such formulations include injectable solutions, tablets, milk, or suspensions, creams, oil-in-water and water-in-oil emulsions, microcapsules and microvesicles.

These compositions will comprise conventional pharmaceutical excipients and carriers typically used in drug formulations, e.g., water, saline solutions, such as phosphate buffered saline, buffers, surfactants.

The subject compounds may be free or entrapped in microcapsules, in colloidal drug delivery systems such as liposomes, microemulsions, and macroemulsions. Suitable materials and methods for preparing pharmaceutical formulations are disclosed in *Remington's Pharmaceutical Chemistry*, 16$^{th}$ Edition, (1980). Also, solid formulations containing the subject compounds, such as tablets, and capsule formulations, may be prepared.

Suitable examples thereof include semipermeable materials of solid hydrophobic polymers containing the subject compound which may be in the form of shaped articles, e.g., films or microcapsules, as well as various other polymers and copolymers known in the art.

The dosage effective amount of compounds according to the invention will vary depending upon factors including the particular compound, toxicity, and inhibitory activity, the condition treated, and whether the compound is administered alone or with other therapies. Typically a dosage effective amount will range from about 0.0001 mg/kg to 1500 mg/kg, more preferably 1 to 1000 mg/kg, more preferably from about 1 to 150 mg/kg of body weight, and most preferably about 50 to 100 mg/kg of body weight.

The subjects treated will typically comprise mammals and most preferably will be human subjects, e.g., human cancer subjects.

The compounds of the invention may be used alone or in combination. Additionally, the treated compounds may be utilized with other types of treatments, e.g., cancer treatments. For example, the subject compounds may be used with other chemotherapies, e.g., tamoxifen, taxol, methothrexate, biologicals, such as antibodies, growth factors, lymphokines, or radiation, etc. Combination therapies may result in synergistic results.

The preferred indication is cancer, especially the cancers identified previously.

While the invention has been described in terms of preferred embodiments, the skilled artisan will appreciate that various modifications, substitutions, omissions and changes may be made without departing from the spirit thereof. Accordingly, it is intended that the scope of the present invention be limited solely by the scope of the following claims, including equivalents thereof.

REFERENCES (1) Mignatti, P.; Rifkin, D. B. Biology and biochemistry of proteinases in tumor invasion *Physiological Reviews* 1993, 73, 161–195.

(2) Westermarck, J.; Kähäri, V. -M. Regulation of matrix metalloproteinase expression in tumor invasion *FASEB J.* 1999, 13, 781–792.

(3) Benaud, C.; Dickson, R. B.; Thompson, E. W. Roles of the Matrix Metalloproteinases in Mammary Gland Development and Cancer *Breast Cancer Res. Treat.* 1998, 50, 97–116.

(4) Oberst, M. D., Lin, C. -Y., Dickson, R. B., and Johnson, M. D. Role of Proteases in Breast Cancer *J. of Women's Cancer* 2000,in pres (5) Takeuchi, T.; Harris, J. L.; Huang, W.; Yan, K. W.; Coughlin, S. R.; Craik, C. S. Cellular Localization of Membrane-type Serine Protease 1 and Identification of Protease-activated Receptor-2 and Single-chain Urokinase-type Plasminogen Activator as Substrates *J. Biol. Chem* 2000, 275, 26333–26342.

(6) Babine, R. E.; Bender, S. L. Molecular recognition of protein-ligand complexes: applications to drug design *Chem. Rev.* 1997, 97, 1359–1472.

(7) Leung, D.; Abbenante, G.; Fairlie, D. P. Protease inhibitors: current status and future prospects *J. Med. Chem.* 2000, 43, 305–341.

(8) Robinson, R. P.; Laird, E. R.; Blake, J. F.; Bordner, J.; Donahue, K. M.; Lopresti-Morrow, L. L.; Mitchell, P. G.; Reese, M. R.; Reeves, L. M.; Stam, E. J.; Yocum, S. A. Structure-based design and synthesis of a potent matrix metalloproteinase-13 inhibitor based on a pyrrolidinone scaffold *J. Med. Chem.* 2000, 43, 2293–2296.

(9) Lin, C. -Y.; Wang, J. -K.; Torri, J.; Dou, L.; Sang, Q. A.; Dickson, R. B. Characterization of a novel, membrane-bound, 80-kda matrix-degrading protease from human breast cancer cells. monoclonal antibody production, isolation, and localization *J. Biol. Chem.* 1997, 272, 9147–9152.

(10) Lin, C. -Y.; Anders, J.; Johnson, M.; Sang, Q. A.; Dickson, R. B. Molecular cloning of cDNA for matriptase, a matrix-degrading serine protease with trypsin-like activity *J. Biol. Chem.* 1999, 274, 18231–18236.

(11) Lin, C. -Y.; Anders, J.; Johnson, M.; Dickson, R. B. Purification and characterization of a complex containing matriptase and a kunitz-type serine protease inhibitor from human milk* *J. Biol. Chem.* 1999, 274, 18237–18242.

(12) Lee, S. -L.; Dickson, R. B.; Lin, C. -Y. Activation of hepatocyte growth factor and urokinase/plasminogen activator by matriptase, an epithelial membrane serine protease. *J. Biol. Chem* 2000, 275, 36720–36725.

(13) Takeuchi, T.; Shuman, M. A.; Craik, C. S. Reverse biochemistry: use of macromolecular protease inhibitors to dissect complex biological processes and identify a membrane-type serine protease in epithelial cancer and normal tissue *Proc. Natl. Acad. Sci. USA* 1999, 96, 11054–11061.

(14) Bernstein, F.; Koetzle, T. F.; Williams, G. J. B.; Meyer Jr, E. F.; Brice, M. D.; Rodgers, J. R.; Kennard, O.; Schimanouchi, T.; Tasumi, M. J. The protein data bank: a computer-based archival file for macromolecular structures *J. Mol. Biol. Chem.* 1977, 112, 535–535.

(15) Sali, A.; Potterton, L.; Yuan, F.; van Vlijmen, H.; Karplus, M. Evaluation of comparative protein modeling by MODELLER *PROTEINS: Structure, Function, and Genetics* 1995, 23, 318–326.

(16) Sali, A. Modeling mutations and homologous proteins *Curr. Opin. Biotech.* 1995, 6, 437–451.

(17) Fersht, A. The Three-Dimensional Structure of Proteins; In *Structure and Mechanism in Protein Science. A Guide to Enzyme Catalysis and Protein Folding;* Julet, M. R., ed. W. H. Freeman: New York, 1999; pp 1–53.

(18) Makino, S.; Kuntz, I. D. Automated flexible ligand docking method and its application for database search *J. Comput. Chem.* 1997, 18, 1812–1825.

(19) Pak, Y.; Wang, S. Application of a molecular dynamics simulation method with a generalized effective potential to the flexible molecular docking problems *J. Phys. Chem. B* 2000, 104, 354–359.

(20) Weber, P. C.; Lee, S. -L.; Lewandowski, F. A.; Schadt, M. C.; Chang, C. -H.; Kettner, C. A. Kinetic and crystallographic studies of thrombin with Ac-(D) Phe-Pro-boroArg-OH and its lysine, Amidine, homolysine, and ornithine analogs *Biochemistry* 1995, 34, 3750–3757.

(21) Altschul, S. F.; Madden, T. L.; Schäffer, A. A.; Zhang, J.; Zhang, Z.; Miller, W.; Lipman, D. J. Gapped BLAST and PSI-BLAST: a new generation of protein database search programs *Nucleic Acids Res.* 1997, 25, 3389–3402.

(22) Brooks, B. R.; Bruccoleri, R. E.; Olafson, B. D.; States, D. J.; Swaminathan, S.; Karplus, M. CHARMM: a program for macromolecular energy, minimization, and dynamics calculations *J. Comput. Chem.* 1983, 4, 187–217.

(23) Brunger, A. T.; Karplus, M. Polar hydrogen positions in proteins: empirical energy placement and neutron diffraction comparison *Proteins: Struct., Funct., Genet.* 1988, 4, 148–156.

(24) Bemis, G. W.; Kuntz, I. D. A fast and efficient method for 2D and 3D molecular shape description *J. Comp.-Aid. Mol. Design* 1992, 6, 607–628.

(25) Durell, S. R.; Brooks, B. R.; Ben-Naim, A. Solvent-induced forces between two hydrophilic groups *J. Phys. Chem.* 1994, 98, 2198–2202.

What is claimed is:

1. A method of inhibiting carcinoma progression comprising administering to a subject an effective amount of a compound selected from the group consisting of compounds (A) to (I)

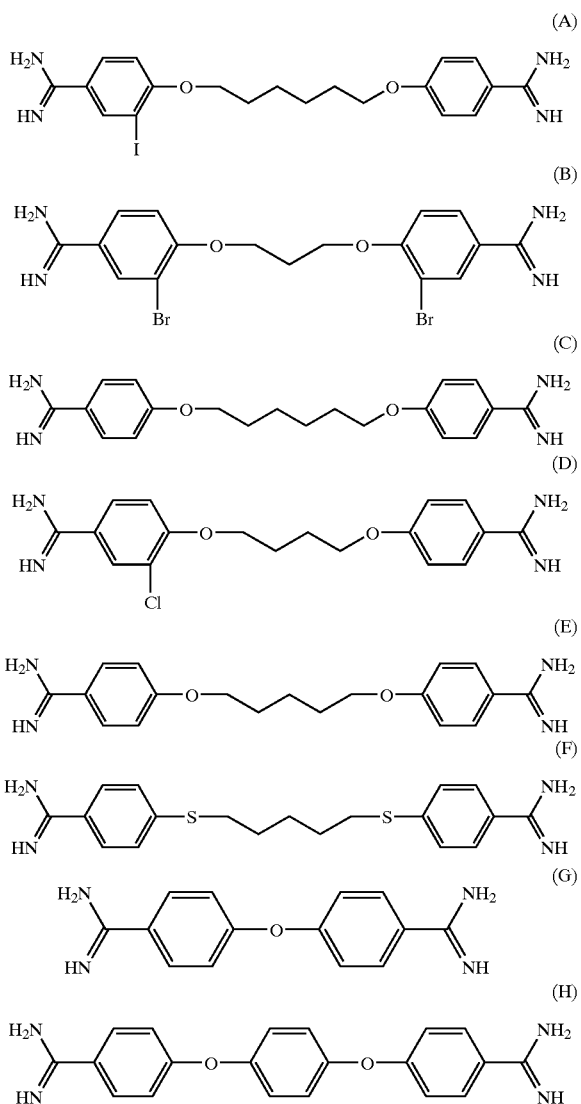

-continued

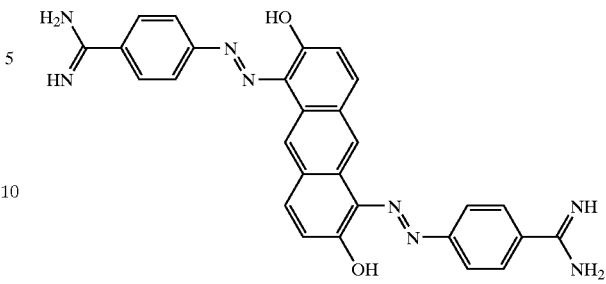

and analogs thereof.

2. The method according to claim 1, wherein at least one of compounds (A) to (I) are administered to the subject in a daily dose of from 0.1 mg to 500 mg for each kilogram of subject weight.

3. The method according to claim 2, wherein compound (A) is administered to the subject in a daily dose of from about 1.0 mg to 200 mg for each kilogram of subject weight.

4. The method according to claim 1, wherein at least one of compounds (A) to (I) inhibit progression related protease cascade.

5. The method according to claim 4, further comprising inhibiting matriptase activity.

6. The method according to claim 5, wherein the inhibiting matriptase activity comprises inhibiting activation of a substrate involved in carcinoma progression.

7. The method according to claim 6, wherein the substrate is an extracellular matrix component, a growth factor, or a protease.

8. The method according to claim 6, wherein the substrate is HGF/SF or pro-uPA.

9. The method according to claim 4, further comprising inhibiting the production of a catalytically active fragment of HGF/SF produced by the cleavage of HGF/SF or uPA produced by the cleavage of pro-uPA.

10. A method of inhibiting matriptase comprising administering to a subject an effective amount of at least one compound selected from the group consisting of compounds (A) to (I)

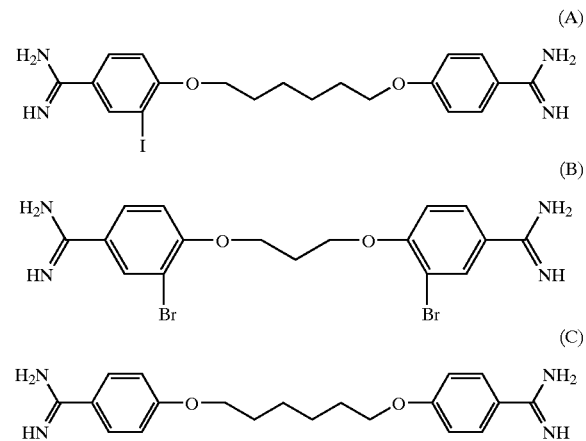

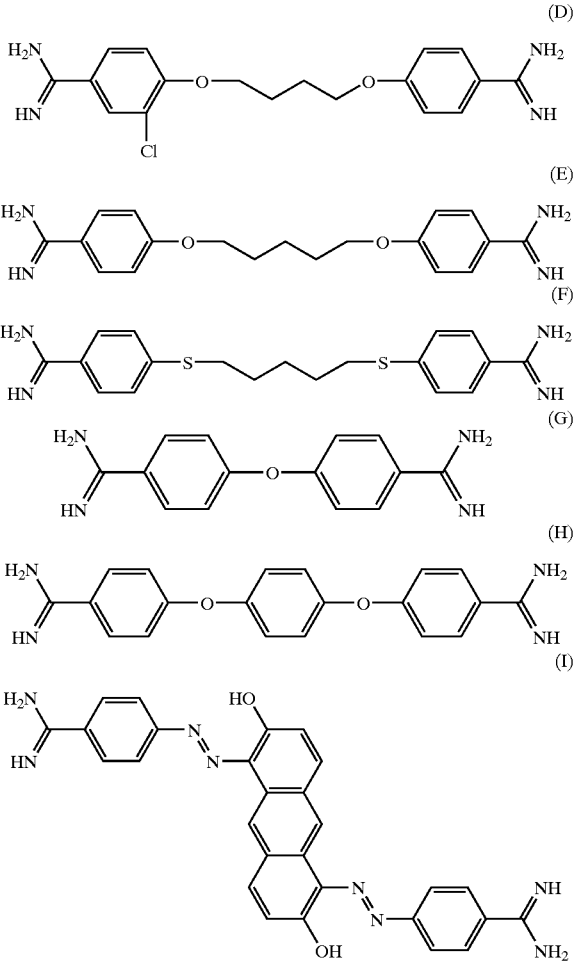

and analogs thereof.

11. The method according to claim 10, wherein the at least one compound antagonizes carcinoma progression related protein cascade.

12. The method according to claim 10, wherein the method results in the inhibition of carcinoma progression.

13. A method of treating cancer comprising administering to a subject an effective amount of at least one compound selected from the group consisting of compounds (A) to (I)

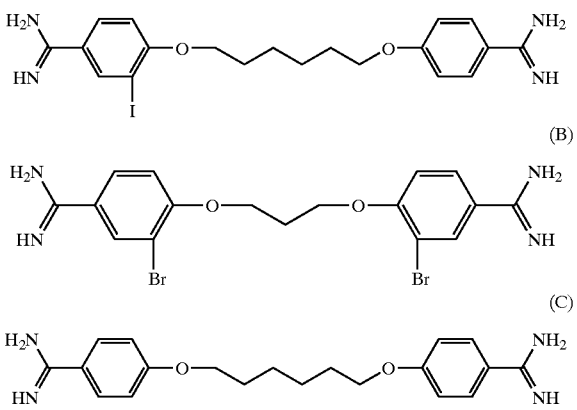

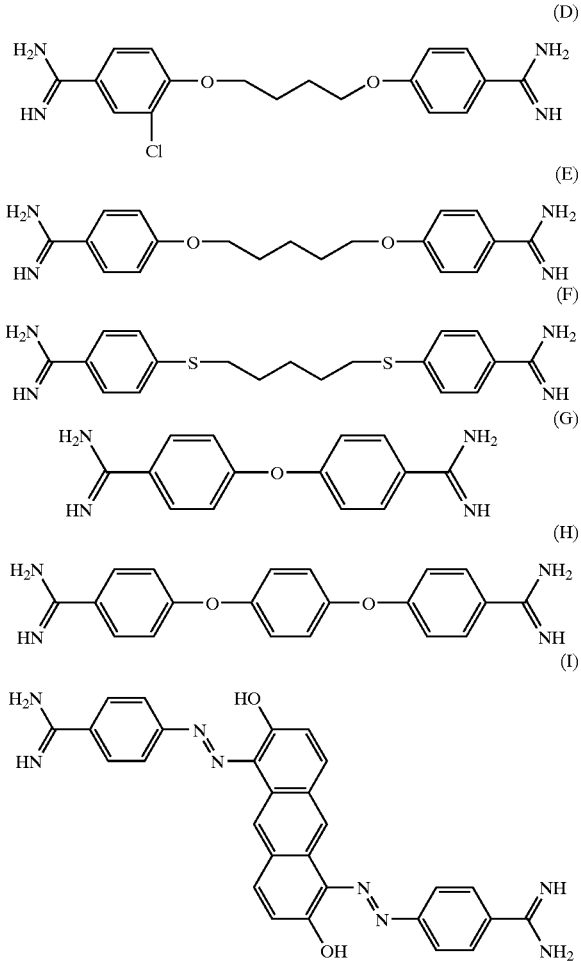

and analogs thereof.

14. The method of claim 13, wherein the cancer is selected from the group consisting of breast, ovarian, prostate, endometrial, colon, pancreatic, head and neck, gastric, renal, brain, and CML.

15. The method of claim 13, wherein the at least one compound is administered by a method selected from the group consisting of oral, intranasal, intraperitoneal, intravenous, intramuscular, intratumoral, rectal, and transdermal.

16. The method of claim 13, wherein the effective amount ranges from 0.01 mg to 200 mg for each kilogram of subject weight.

17. The method of claim 13, wherein the effective amount ranges from 0.5 mg to 50 mg for each kilogram of subject weight.

18. The method of claim 13, further comprising administration of an anticancer compound, radiation, or a compound that induced apoptosis.

19. A pharmaceutical composition comprising a therapeutically effective amount of a compound selected from the group consisting of compounds (A) to (I)

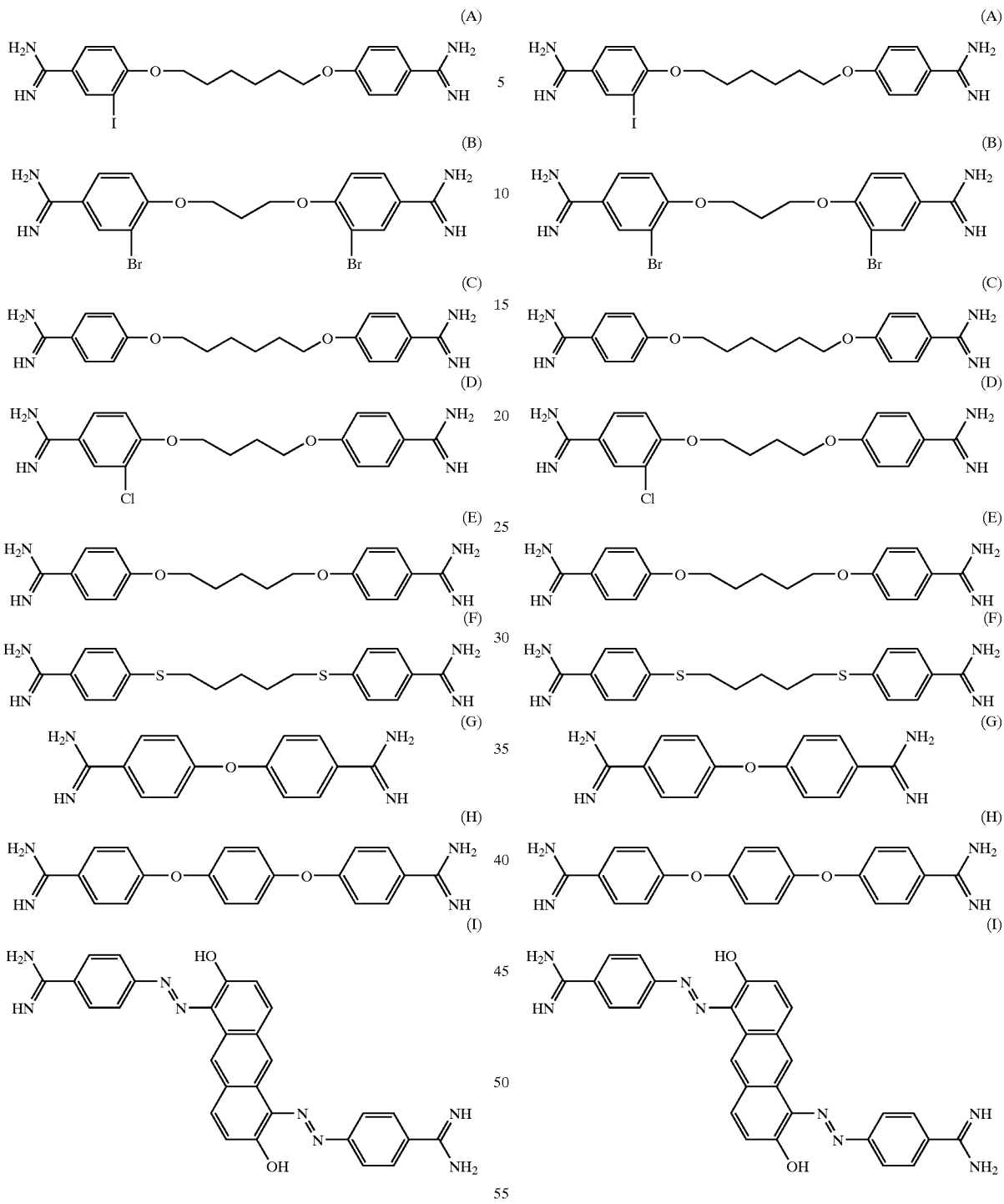

and analogs thereof, and a pharmaceutically acceptable carrier.

20. The composition of claim 19, which is suitable for administration via injection, orally, transdermally, intranasally, intraocularly, or rectally.

21. A method of treating a malignancy, a pre-malignant condition, or a pathologic condition in a subject which is characterized by the expression of single-chain (zymogen) and/or two-chain (activated) form of matriptase, the method comprising administering a therapeutically effective amount of a compound selected from the group consisting of compounds (A) to (I)

and analogs thereof.

22. The method of claim 21, wherein the malignancy and the pre-malignant condition is a condition of the breast.

23. The method of claim 21, wherein the pre-malignant condition is selected from the group consisting of a typical ductal hyperplasia of the breast, actinic keratosis, leukoplakia, Barrett's epithelium (columnar metaplasia) of the esophagus, ulcerative colitis, adenomatous colorectal polyps, erythroplasia of Queyrat, Bowen's disease, bowenoid papulosis, vulvar intraepthelial neoplasia, and displastic changes to the cervix.

* * * * *